(12) United States Patent
Binch et al.

(10) Patent No.: US 8,367,690 B2
(45) Date of Patent: Feb. 5, 2013

(54) AMINOPYRIDINE DERIVATIVES HAVING AURORA A SELECTIVE INHIBITORY ACTION

(75) Inventors: Hayley Binch, Encinitas, CA (US); Masaya Hashimoto, Tsukuba (JP); Michael Mortimore, Abington (GB); Mitsuru Ohkubo, Ushiku (JP); Tomoko Sunami, Tokai-mura (JP)

(73) Assignees: Vertex Pharmaceuticals Inc., Cambridge, MA (US); MSD K.K., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/259,620

(22) PCT Filed: Mar. 15, 2010

(86) PCT No.: PCT/US2010/027279
§ 371 (c)(1),
(2), (4) Date: Sep. 23, 2011

(87) PCT Pub. No.: WO2010/111056
PCT Pub. Date: Sep. 30, 2010

(65) Prior Publication Data
US 2012/0015969 A1 Jan. 19, 2012

Related U.S. Application Data

(60) Provisional application No. 61/162,727, filed on Mar. 24, 2009.

(51) Int. Cl.
*A01N 43/54* (2006.01)
*A61K 31/505* (2006.01)

(52) U.S. Cl. ........................ 514/275; 544/324
(58) Field of Classification Search .................. 544/324; 514/275
See application file for complete search history.

(56) References Cited

U.S. PATENT DOCUMENTS

| 2003/0055044 A1 * | 3/2003 | Davies et al. ............. 514/217.05 |
| 2007/0179125 A1 | 8/2007 | Fraysse et al. |
| 2007/0270444 A1 | 11/2007 | Bebbington et al. |
| 2012/0029004 A1 * | 2/2012 | Binch et al. .................. 514/275 |

FOREIGN PATENT DOCUMENTS

| WO | 0222601 A1 | 3/2002 |
| WO | WO 0222601 A1 * | 3/2002 |
| WO | WO 0222602 A2 * | 3/2002 |
| WO | 2005040159 A1 | 5/2005 |
| WO | 2010111050 A1 | 9/2010 |
| WO | 2011019405 A1 | 2/2011 |

* cited by examiner

*Primary Examiner* — James O Wilson
*Assistant Examiner* — Alexander R Pagano
(74) *Attorney, Agent, or Firm* — Yong Zhao; David A. Muthard; Matthew A. Leff

(57) ABSTRACT

The present invention relates to a compound of Formula (I): wherein: $R^1$ is H, —NHCOOR$^{1a}$, $C_{5-6}$ cycloalkyl, or phenyl; where the cycloalkyl and phenyl each independently may be substituted with one to three of the same or different substituents selected from $R^{10}$; $R^{1a}$ is $C_{1-3}$ alkyl which may be substituted with one to three of the same or different substituents selected from F and Cl; $R^2$ is H, —COOH, —CH$_2$COOH, —COOR$^{2a}$, or —CH$_2$COOR$^{2a}$; $R^{2a}$ is $C_{1-2}$ alkyl, where the alkyl may be substituted with one to three of the same or different substituents selected from halogen atoms; $R^3$ is H, $C_{1-6}$ alkyl, where the alkyl may be substituted with one to three of the same or different substituents selected from $R^{11}$; $R^{10}$ is F, Cl, CF$_3$, or $C_{1-2}$ alkyl; $R^{11}$ is halogen atom, hydroxy, or cyano; W is selected from: $W^{2a}$ is H, halogen atom, cyano, $C_{1-2}$ alkyl, or $C_{3-5}$ cycloalkyl, or a pharmaceutically acceptable salt or ester thereof.

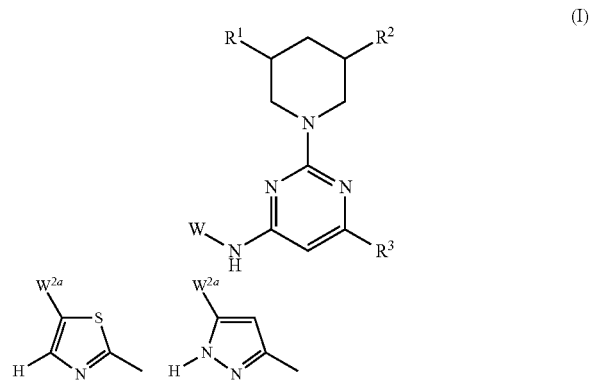

6 Claims, No Drawings

AMINOPYRIDINE DERIVATIVES HAVING AURORA A SELECTIVE INHIBITORY ACTION

TECHNICAL FIELD

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

REFERENCE TO SEQUENCE LISTING SUBMITTED ELECTRONICALLY

The sequence listing of the present application is being submitted electronically via EFS-Web as an ASCII formatted sequence listing with a file name "BANONC00019USPCT-SEQTXT-22SEPT2011.txt", creation date of Sep. 22, 2011 and a size of 895 bytes. This sequence listing submitted via EFS-Web is part of the specification and is herein incorporated by reference in its entirety.

BACKGROUND ART

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

On the other hand, patent applications concerning compounds having an Aurora kinase inhibiting action have been previously filed (WO2002/022606, WO2002/022602, WO2002/0220601, WO2006/046734).

DISCLOSURE OF THE INVENTION

The purpose of the present invention is to provide novel aminopyridine derivatives which show an excellent Aurora A selective inhibitory action and cell-growth inhibitory action based on the foregoing, thereby achieving a synergistic action by a combined use with other antitumor agent(s).

The present inventors have synthesized a variety of novel aminopyridine derivatives and found that the compound represented by the following Formula (I) shows an excellent Aurora A selective inhibitory action.

Thus the invention relates to a compound of Formula (I):

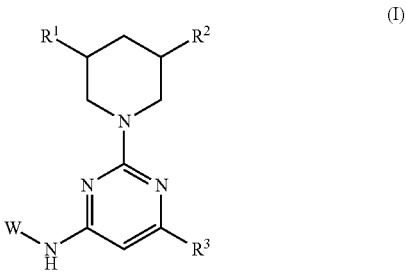

wherein:
$R^1$ is H, —NHCOOR$^{1a}$, $C_{5-6}$ cycloalkyl, or phenyl, where the cycloalkyl and phenyl each independently may be substituted with one to three of the same or different substituents selected from $R^{10}$;
$R^{1a}$ is $C_{1-3}$ alkyl which may be substituted with one to three of the same or different substituents selected from F and Cl;
$R^2$ is H, —COOH, —CH$_2$COOH, —COOR$^{2a}$, or —CH$_2$COOR$^{2a}$;
$R^{2a}$ is $C_{1-2}$ alkyl, where the alkyl may be substituted with one to three of the same or different substituents selected from halogen atoms;
$R^3$ is H or $C_{1-6}$ alkyl, where the alkyl may be substituted with one to three of the same or different substituents selected from $R^{11}$;
$R^{10}$ is F, Cl, CF$_3$, or $C_{1-2}$ alkyl;
$R^{11}$ is halogen atom, hydroxy, or cyano;
W is selected from:

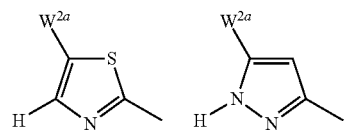

$W^{2a}$ is H, halogen atom, cyano, $C_{1-2}$ alkyl, or $C_{3-5}$ cycloalkyl,
or a pharmaceutically acceptable salt or ester thereof.

The invention also relates to a combined preparation for simultaneous, separate or sequential administration in the treatment of cancer, comprising two separate preparations which are:
(i) a preparation comprising, together with a pharmaceutically acceptable carrier or diluent, a compound represented by the above-described Formula (I) or a pharmaceutically acceptable salt or ester thereof; and
(ii) a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:

the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;

the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;

the antitumor antibiotic is actinomycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;

the plant-derived antitumor agent is vincristine, vinblastine, vindesine, etoposide, sobuzoxane, docetaxel, paclitaxel or vinorelbine;

the antitumor platinum coordination compound is cisplatin, carboplatin, nedaplatin or oxaliplatin;

the antitumor camptothecin derivative is irinotecan, topotecan or camptothecin;

the antitumor tyrosine kinase inhibitor is gefitinib, imatinib, sorafenib, sunitinib, dasatinib, or erlotinib;

the monoclonal antibody is cetuximab, rituximab, bevacizumab, alemtuzumab or trastuzumab;

the interferon is interferon α, interferon α-2a, interferon α-2b, interferon β, interferon γ-1a or interferon γ-n1;

the biological response modifier is krestin, lentinan, sizofiran, picibanil or ubenimex; and the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "alkyl" is intended to include both branched and straight-chain saturated aliphatic hydrocarbon groups having the specified number of carbon atoms. For example, $C_{1-6}$, as in the term "$C_{1-6}$ alkyl" is defined to include groups having 1, 2, 3, 4, 5, or 6 carbons in a linear or branched arrangement. For example, the term "$C_{1-6}$ alkyl" specifically includes methyl, ethyl, n-propyl, i-propyl, n-butyl, t-butyl, i-butyl, pentyl, hexyl, and so on. Generally, the term "$C_{m-n}$ alkyl" is defined to include groups having m to n carbons in a linear or branched arrangement, where m and n each independently are an integer of 1 to 6 but n is greater than m.

The term "cycloalkyl" means a monocyclic saturated aliphatic hydrocarbon group having the specified number of carbon atoms. For example, the term "$C_{3-8}$ cycloalkyl" includes cyclopropyl, methyl-cyclopropyl, cyclobutyl, 2,2-dimethyl-cyclobutyl, 2-ethyl-cyclopentyl, cyclohexyl, cyclohexyl, cycloheptyl, cyclooctyl, and so on. In an embodiment of the invention the term "cycloalkyl" includes the groups described immediately above and further includes monocyclic unsaturated aliphatic hydrocarbon groups. For example, the term "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "halogen atom" in the above Formula (I) is, for example, fluorine atom, chlorine atom, bromine atom or iodine atom. Among them, for example, fluorine atom, chlorine atom or bromine atom is preferred.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovorin.

Here, in the above-mentioned combined preparation, either or both of the two separate preparations may be an oral preparation; and also one may be an oral preparation, while another may be a parental preparation (injections or drip infusions).

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known, Preferably, oral preparations, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably oral administration. Thus, when a combined preparation is administered, both administrations may be parenteral; one administration may be parenteral while the other may be oral; or both administrations may be oral. Preferably, both preparations in the combined preparation are administered orally. Here, the term "parenteral administration" is, for example, intravenous administration, subcutaneous administration or intramuscular administration, and preferably it is intravenous administration. Even when three or more preparations are combined and administered, every preparation may be orally administered.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel or docetaxel, preferably paclitaxel or docetaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms or by organic synthesis and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The teem "plant-derived antitumor agent" may be exemplified by vincristine, vinblastine, vindesine, etoposide, sobuzoxane, docetaxel, paclitaxel and vinorelbine, and preferred and docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "antitumor platinum coordination (platinum-complex) compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediamine-malonatoplatinum (II); aqua(1,2-diaminodicyclohexane) sulfatoplatinum (II); aqua(1,2-diaminocyclohexane)malonatoplatinum (II); (1,2-diaminocyclohexane) malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers a γ-phosphate group of ATP to a hydroxy group of a specific tyrosine in protein. The term "antitumor tyrosine kinase inhibitor" may be exemplified by gefitinib, imatinib, sorafenib, sunitinib, dasatinib, or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofiran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from Glaxo-SmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tadename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); sorafenib from Bayer as Nexavar (tradename); sunitinib from Pfizer as Sutent (tradename); dasatinib from Bristol Myers Squibb as Sprycel (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofiran from Kaken Seiyaku Co., Ltd. as Sonifiran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group or a pyridine analogue group, any of which is substituted with an amino group. It is exemplified by a compound of the above Formula (I), and preferably any one compound of the below-mentioned (a) to (z): a compound which is:

(a) methyl trans-5-[(cert-butoxycarbonyl)amino]-1-[4-methyl-6-(1H-pyrazol-5-ylamino)pyrimidin-2-yl]piperidine-3-carboxylate;
(b) trans-5-[(tert-butoxycarbonyl)amino]-1-[4-methyl-6-(1H-pyrazol-5-ylamino)pyrimidin-2-yl]piperidine-3-carboxylic acid;
(c) methyl cis-5-[(tert-butoxycarbonyl)amino]-1-[4-methyl-6-(1H-pyrazol-5-ylamino)pyrimidin-2-yl]piperidine-3-carboxylate;
(d) cis-5-[(tert-butoxycarbonyl)amino]-1-[4-methyl-6-(1H-pyrazol-5-ylamino)pyrimidin-2-yl]piperidine-3-carboxylic acid;
(e) methyl trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylate;
(f) trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;
(g) methyl cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;
(h) cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;
(i) methyl cis-1-[4-methyl-6-(1H-pyrazol-5-ylamino)pyrimidin-2-yl]-5-phenylpiperidine-3-carboxylate;
(j) cis-1-[4-methyl-6-(1H-pyrazol-5-ylamino)pyrimidin-2-yl]-5-phenylpiperidine-3-carboxylic acid;
(k) methyl cis-1-[4-methyl-6-(1H-pyrazol-5-ylamino)pyrimidin-2-yl]-5-[3-(trifluoromethyl)phenyl]piperidine-3-carboxylate;
(l) cis-1-[4-methyl-6-(1H-pyrazol-5-ylamino)pyrimidin-2-yl]-5-[3-(trifluoromethyl)phenyl]piperidine-3-carboxylic acid;
(m) methyl cis-5-cyclohexyl-1-[4-methyl-6-(1H-pyrazol-5-ylamino)pyrimidin-2-yl]piperidine-3-carboxylate;
(n) cis-5-cyclohexyl-1-[4-methyl-6-(1H-pyrazol-5-ylamino)pyrimidin-2-yl]piperidine-3-carboxylic acid;
(o) methyl cis-5-cyclohexyl-1-[4-methyl-6-(1,3-thiazol-2-ylamino)pyrimidin-2-yl]piperidine-3-carboxylate;
(p) cis-5-cyclohexyl-1-[4-methyl-6-(1,3-thiazol-2-ylamino)pyrimidin-2-yl]piperidine-3-carboxylic acid;
(q) methyl cis-1-{4-[(5-cyano-1,3-thiazol-2-yl)amino]-6-methylpyrimidin-2-yl}-5-cyclohexylpiperidine-3-carboxylate;
(r) cis-1-{4-[(5-cyano-1,3-thiazol-2-yl)amino]-6-methylpyrimidin-2-yl}-5-cyclohexylpiperidine-3-carboxylic acid;
(s) methyl cis-5-cyclohexyl-1-{4-[(5-cyclopropyl-1,3-thiazol-2-yl)amino]-6-methylpyrimidin-2-yl}piperidine-3-carboxylate;
(t) cis-5-cyclohexyl-1-{4-[(5-cyclopropyl-1,3-thiazol-2yl)amino]-6-methylpyrimidin-2-yl}piperidine-3-carboxylic acid;
(u) methyl cis-5-cyclohexyl-1-{4-[(3-cyclopropyl-1H-pyrazol-5-yl)amino]-6-methylpyrimidin-2-yl}piperidine-3-carboxylate;
(v) cis-5-cyclohexyl-1-{4-[(3-cyclopropyl-1H-pyrazol-5-yl)amino]-6-methylpyrimidin-2-yl}piperidine-3-carboxylic acid;
(w) methyl (cis-5-cyclohexyl-1-{4-[(3-cyclopropyl-1H-pyrazol-5-yl)amino]-6-methylpyrimidin-2-yl}piperidin-3-yl)acetate;
(x) (cis-5-cyclohexyl-1-{4-[(3-cyclopropyl-1H-pyrazol-5-yl)amino]-6-methylpyrimidin-2-yl}piperidin-3-yl)acetic acid;
(y) methyl {cis-5-cyclohexyl-1-[4-methyl-6-(1,3-thiazol-2-ylamino)pyrimidin-2-yl]piperidin-3-yl}acetate, or
(z) {cis-5-cyclohexyl-1-[4-methyl-6-(1,3-thiazol-2-ylamino)pyrimidin-2-yl]piperidin-3-yl}acetic acid,
or a pharmaceutically acceptable salt or ester thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

Embodiments of the compound represented by the above Formula (I) will be illustrated in more detail.

$R^1$ is H, —NHCOOR$^{1a}$, $C_{5-6}$ cycloalkyl, or phenyl, where the cycloalkyl and phenyl each independently may be substituted with one to three of the same or different substituents selected from $R^{10}$.

Preferably, $R^1$ is —NHCOOR$^{1a}$, cyclohexyl, or phenyl, where the cyclohexyl and phenyl each independently may be substituted with one to three of the same or different substituents selected from $R^{10}$.

$R^{1a}$ is $C_{1-3}$ alkyl which may be substituted with one to three of the same or different substituents selected from F and Cl.

Preferably, $R^{1a}$ is methyl, ethyl, propyl, isopropyl, or t-butyl, any of which may be substituted with one to three of fluorine atoms.

$R^2$ is H, —COOH, —CH$_2$ COOH, —COOR$^{2a}$, or —CH$_2$COOR$^{2a}$.

Preferably, $R^2$ is —COOH or —CH$_2$ COOH.

$R^{2a}$ is $C_{1-2}$ alkyl, where the alkyl may be substituted with one to three of the same or different substituents selected from halogen atoms;

Preferably, $R^{2a}$ is methyl.

$R^3$ is H or $C_{1-6}$ alkyl, where the alkyl may be substituted with one to three of the same or different substituents selected from $R^{11}$.

Preferably, $R^3$ is methyl.

$R^{10}$ is F, Cl, $CF_3$, or $C_{1-2}$ alkyl.

Preferably, $R^{10}$ is F or Cl.

$R^{11}$ is halogen atom, hydroxy, or cyano.

Preferably, $R^{11}$ is halogen atom.

W is selected from:

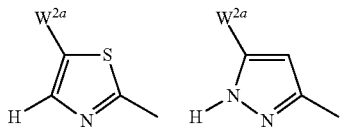

$W^{2a}$ is H, halogen atom, cyano, $C_{1-2}$ alkyl, or $C_{3-5}$ cycloalkyl.

Preferably, $W^{2a}$ is H, cyano, or cyclopropyl.

Further, in the combined preparation comprising two separate preparations according to the invention, preferably either or both of the two separate preparations are an oral preparation.

The combined preparation comprising two separate preparations according to the invention is preferably such that one of the preparations is a preparation containing, together with a pharmaceutically acceptable carrier or diluent, the following:

(a) methyl trans-5-[(tert-butoxycarbonyl)amino]-1-[4-methyl-6-(1H-pyrazol-5-ylamino)pyrimidin-2-yl]piperidine-3-carboxylate;

(b) trans-5-[(tert-butoxycarbonyl)amino]-1-[4-methyl-6-(1H-pyrazol-5-ylamino)pyrimidin-2-yl]piperidine-3-carboxylic acid;

(c) methyl cis-5-[(tert-butoxycarbonyl)amino]-1-[4-methyl-6-(1H-pyrazol-5-ylamino)pyrimidin-2-yl]piperidine-3-carboxylate;

(d) cis-5-[(tert-butoxycarbonyl)amino]-1-[4-methyl-6-(1H-pyrazol-5-ylamino)pyrimidin-2-yl]piperidine-3-carboxylic acid;

(e) methyl trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylate;

(f) trans-1-[4-methyl-6-(1H-pyrazol-5-ylamino)pyrimidin-2-yl]-5-[{([(2S)-1,1,1-trifluoropropan-2-yl]oxy}carbonyl)amino]piperidine-3-carboxylic acid;

(g) methyl cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(h) cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(i) methyl cis-1-[4-methyl-6-(1H-pyrazol-5-ylamino)pyrimidin-2-yl]-5-phenylpiperidine-3-carboxylate;

(j) cis-1-[4-methyl-6-(1H-pyrazol-5-ylamino)pyrimidin-2-yl]-5-phenylpiperidine-3-carboxylic acid;

(k) methyl cis-1-[4-methyl-6-(1H-pyrazol-5-ylamino)pyrimidin-2-yl]-5-[3-(trifluoromethyl)phenyl]piperidine-3-carboxylate;

(l) cis-1-[4-methyl-6-(1H-pyrazol-5-ylamino)pyrimidin-2-yl]-5-[3-(trifluoromethyl)phenyl]piperidine-3-carboxylic acid;

(m) methyl cis-5-cyclohexyl-1-[4-methyl-6-(1H-pyrazol-5-ylamino)pyrimidin-2-yl]piperidine-3-carboxylate;

(n) cis-5-cyclohexyl-1-[4-methyl-6-(1H-pyrazol-5-ylamino)pyrimidin-2-yl]piperidine-3-carboxylic acid;

(o) methyl cis-5-cyclohexyl-1-[4-methyl-6-(1,3-thiazol-2-ylamino)pyrimidin-2-yl]piperidine-3-carboxylate;

(p) cis-5-cyclohexyl-1-[4-methyl-6-(1,3-thiazol-2-ylamino)pyrimidin-2-yl]piperidine-3-carboxylic acid;

(q) methyl cis-1-{4-[(5-cyano-1,3-thiazol-2-yl)amino]-6-methylpyrimidin-2-yl}-5-cyclohexylpiperidine-3-carboxylate;

(r) cis-1-{4-[(5-cyano-1,3-thiazol-2-yl)amino]-6-methylpyrimidin-2-yl}-5-cyclohexylpiperidine-3-carboxylic acid;

(s) methyl cis-5-cyclohexyl-1-{4-[(5-cyclopropyl-1,3-thiazol-2-yl)amino]-6-methylpyrimidin-2-yl}piperidine-3-carboxylate;

(t) cis-5-cyclohexyl-1-{4-[(5-cyclopropyl-1,3-thiazol-2-yl)amino]-6-methylpyrimidin-2-yl}piperidine-3-carboxylic acid;

(u) methyl cis-5-cyclohexyl-1-{4-[(3-cyclopropyl-1H-pyrazol-5-yl)amino]-6-methylpyrimidin-2-yl}piperidine-3-carboxylate;

(v) cis-5-cyclohexyl-1-{4-[(3-cyclopropyl-1H-pyrazol-5-yl)amino]-6-methylpyrimidin-2-yl}piperidine-3-carboxylic acid;

(w) methyl (cis-5-cyclohexyl-1-{4-[(3-cyclopropyl-1H-pyrazol-5-yl)amino]-6-methylpyrimidin-2-yl}piperidin-3-yl)acetate;

(x) (cis-5-cyclohexyl-1-{4-[(3-cyclopropyl-1H-pyrazol-5-yl)amino]-6-methylpyrimidin-2-yl}piperidin-3-yl)acetic acid;

(y) methyl {cis-5-cyclohexyl-1-[4-methyl-6-(1,3-thiazol-2-ylamino)pyrimidin-2-yl]piperidin-3-yl}acetate, or (z) {cis-5-cyclohexyl-1-[4-methyl-6-(1,3-thiazol-2-ylamino)pyrimidin-2-yl]piperidin-3-yl}acetic acid, or a pharmaceutically acceptable salt or ester thereof; and the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains, together with a pharmaceutically acceptable carrier or diluent, the following:

(a) methyl trans-5-[(tert-butoxycarbonyl)amino]-1-[4-methyl-6-(1H-pyrazol-5-ylamino)pyrimidin-2-yl]piperidine-3-carboxylate;

(b) trans-5-[(tert-butoxycarbonyl)amino]-1-[4-methyl-6-(1H-pyrazol-5-ylamino)pyrimidin-2-yl]piperidine-3-carboxylic acid;

(c) methyl cis-5-[(tert-butoxycarbonyl)amino]-1-[4-methyl-6-(1H-pyrazol-5-ylamino)pyrimidin-2-yl]piperidine-3-carboxylate;

(d) cis-5-[(tert-butoxycarbonyl)amino]-1-[4-methyl-6-(1H-pyrazol-5-ylamino)pyrimidin-2-yl]piperidine-3-carboxylic acid;

(e) methyl trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylate;

(f) trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(g) methyl cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(h) cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(i) methyl cis-1-[4-methyl-6-(1H-pyrazol-5-ylamino)pyrimidin-2-yl]-5-phenylpiperidine-3-carboxylate;

(j) cis-1-[4-methyl-6-(1H-pyrazol-5-ylamino)pyrimidin-2-yl]-5-phenylpiperidine-3-carboxylic acid;

(k) methyl cis-1-[4-methyl-6-(1H-pyrazol-5-ylamino)pyrimidin-2-yl]-5-[3-(trifluoromethyl)phenyl]piperidine-3-carboxylate;

(l) cis-1-[4-methyl-6-(1H-pyrazol-5-ylamino)pyrimidin-2-yl]-5-[3-(trifluoromethyl)phenyl]piperidine-3-carboxylic acid;

(m) methyl cis-5-cyclohexyl-1-[4-methyl-6-(1H-pyrazol-5-ylamino)pyrimidin-2-yl]piperidine-3-carboxylate;

(n) cis-5-cyclohexyl-1-[4-methyl-6-(1H-pyrazol-5-ylamino)pyrimidin-2-yl]piperidine-3-carboxylic acid;

(o) methyl cis-5-cyclohexyl-1-[4-methyl-6-(1,3-thiazol-2-ylamino)pyrimidin-2-yl]piperidine-3-carboxylate;

(p) cis-5-cyclohexyl-1-[4-methyl-6-(1,3-thiazol-2-ylamino)pyrimidin-2-yl]piperidine-3-carboxylic acid;

(q) methyl cis-1-{4-[(5-cyano-1,3-thiazol-2-yl)amino]-6-methylpyrimidin-2-yl}-5-cyclohexylpiperidine-3-carboxylate;

(r) cis-1-{4-[(5-cyano-1,3-thiazol-2-yl)amino]-6-methylpyrimidin-2-yl}-5-cyclohexylpiperidine-3-carboxylic acid;

(s) methyl cis-5-cyclohexyl-1-{4-[(5-cyclopropyl-1,3-thiazol-2-yl)amino]-6-methylpyrimidin-2-yl}piperidine-3-carboxylate;

(t) cis-5-cyclohexyl-1-{4-[(5-cyclopropyl-1,3-thiazol-2-yl)amino]-6-methylpyrimidin-2-yl}piperidine-3-carboxylic acid;

(u) methyl cis-5-cyclohexyl-1-{4-[(3-cyclopropyl-1H-pyrazol-5-yl)amino]-6-methylpyrimidin-2-yl}piperidine-3-carboxylate;

(v) cis-5-cyclohexyl-1-{4-[(3-cyclopropyl-1H-pyrazol-5-yl)amino]-6-methylpyrimidin-2-yl}piperidine-3-carboxylic acid;

(w) methyl (cis-5-cyclohexyl-1-{4-[(3-cyclopropyl-1H-pyrazol-5-yl)amino]-6-methylpyrimidin-2-yl}piperidin-3-yl)acetate;

(x) (cis-5-cyclohexyl-1-{4-[(3-cyclopropyl-1H-pyrazol-5-yl)amino]-6-methylpyrimidin-2-yl}piperidin-3-yl)acetic acid;

(y) methyl {cis-5-cyclohexyl-1-[4-methyl-6-(1,3-thiazol-2-ylamino)pyrimidin-2-yl]piperidin-3-yl}acetate, or (z) {cis-5-cyclohexyl-1-[4-methyl-6-(1,3-thiazol-2-ylamino)pyrimidin-2-yl]piperidin-3-yl}acetic acid, or a pharmaceutically acceptable salt or ester thereof; and paclitaxel or docetaxel, or a pharmaceutically acceptable salt or ester thereof, together with a pharmaceutically acceptable carrier or diluent.

Description of the process for preparation of compound of Formula (I)
Step 1: Amination

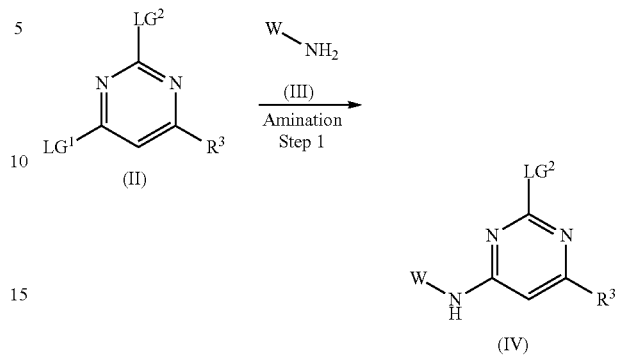

The present process is a method of subjecting Compound (II) (wherein $LG^1$ and $LG^2$ represents a leaving group such as halogen atom or methanesulfonyoxy, and $R^3$ have the same meaning as the symbols for the above Formula (I)) and Compound (III) (wherein W have the same meaning as the symbols for the above Formula (I)) to an amination reaction, to produce Compound (IV) (wherein $LG^2$ is as defined above, and W and $R^3$ have the same meaning as the symbols for the above Formula (I)).

The amination reaction used in this process employs methods well known to those skilled in the art. In the amination reaction used in the process, for example, synthesis can be performed by reacting the above-mentioned Compound (II) and Compound (III) in a solvent such as 1,4-dioxane, 1,2-dimethoxyethane, tetrahydrofuran, methylene chloride, chloroform or toluene, using a palladium catalyst such as tris-dibenzylideneacetone dipalladium (0) or palladium acetate, a ligand such as 2,2'-bisdiphenylphosphino-1,1'-binaphthyl or 4,5-bis(diphenylphosphino)-9,9-dimethylxanthene, and a base such as cesium carbonate or sodium t-butoxide, to afford Compound (IV). Alternatively, Compound (IV) can be obtained by reacting Compound (II) and Compound (III) in a solvent such as N,N-dimethylformamide, N,N-dimethylacetamide, N-methylpyrrolidone or dimethylsulfoxide, in the presence of a base such as triethylamine or diisopropylethylamine, and a additive such as sodium iodide.

Step 2; Further Amination

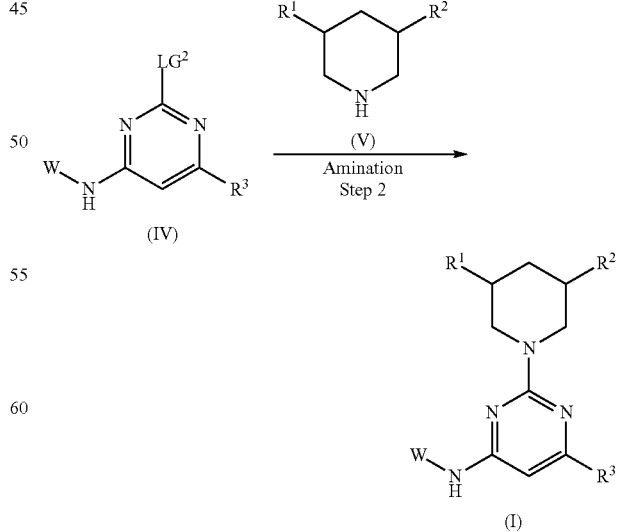

The present process is a method of subjecting Compound (IV) as obtained by the above-described Amination Step 1

(wherein LG² represents a leaving group such as halogen atom or methanesulfonyoxy, and W and R³ have the same meaning as the symbols for the above Formula (I)) and Compound (V) (wherein R¹ and R² have the same meaning as the symbols for the above Formula (I)) to further amination reaction, to produce Compound (I).

The amination reaction used in this process employs methods well known to those skilled in the art. In the amination reaction used in the process, for example, synthesis can be performed by reacting the above-mentioned Compound (IV) and Compound (V) in a solvent such as N,N-dimethylformamide, N,N-dimethylacetamide, N-methylpyrrolidone or dimethylsulfoxide, in the presence of a base such as triethylamine or diisopropylethylamine.

Step 3: Reduction

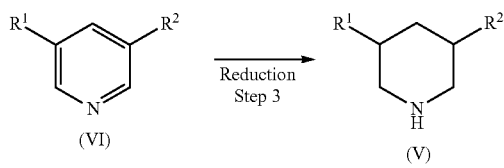

Step 3 refers to a method of preparing the piperidine derivative represented by Formula (V) ("Compound (V)") by catalytic hydrogenation reaction of the pyridine derivative represented by Formula (VI) ("Compound (VI)") that have suitable substituents R¹ and R² at the 3- and 5-positions (wherein R¹ and R² have the same meaning as the symbols for the above Formula (I)).

The catalytic hydrogenation reaction used in this process employs methods well known to those skilled in the art. In the catalytic hydrogenation used in the process, for example, synthesis can be performed by reacting the above-mentioned Compound (VI) in a solvent such as tetrahydrofuran, ethyl acetate, methanol, ethanol or acetic acid, using a palladium catalyst such as palladium (0) black, palladium (0) on charcoal, palladium (0) on alumina, rhodium (0) on charcoal or rhodium (0) on alumina under normal or supercharged pressure, to afford Compound (V).

Compounds (VI) can be prepared using methods well known to those skilled in the art from commercially available compounds.

Before or after Step 2, further modifications of R¹ or R² can be performed by the methods well known to those skilled in the art Next, the Aurora A and Aurora B inhibitory actions of the compound of Formula (I) according to the invention will be explained below.

Aurora A Inhibitory Activity (1) Purification of Aurora A cDNA of N-terminal His-tagged human Aurora A was integrated into an expression vector, which was then highly expressed in *Escherichia coli* BL21-CodonPlus(DE3)-RIL cells. The *Escherichia coli* was harvested and lysed, and then the His-tagged human Aurora A protein was applied onto a nickel chelate column and eluted from the column with imidazole. The active fractions were desalted with a desalting column to give a purified enzyme.

(2) Measurement of Activity of Aurora A

For measurement of the activity of Aurora A, the substrate used was a synthetic peptide (5-FAM (5-carboxyfluorescein)-γ-aminobutyric acid-Ala-Leu-Arg-Arg-Ala-Ser-Leu-Gly-NH₂) (SEQ.ID.NO.:1), which was purchased from Toray Research Center, Inc.

For the phosphorylation reaction, the method by Upstate, Inc. [Kinase Profiler™ Assay Protocols] was referred to, and phosphorylation of the substrate was detected using IMAP® technology (Molecular Devices, Co. Ltd.) (Gaudet E W. et. al, J. Biomol. Screen, 8, 164-175(2003)). Concretely, the phosphorylation reaction and the detection were carried out as follows:

The phosphorylation reaction was conducted using 384 well plate, and the reaction volume was 10 μl/well. The reaction buffer is comprised of 50 mM Tris-chloride buffer (pH 7.4), 15 mM magnesium acetate, and 0.2 mM ethylenediamine-N,N,N',N'-tetraacetic acid (EDTA). Thereto, the purified Aurora A protein, 100 nM of the peptide substrate, and 20 μM of adenosine 5'-triphosphate (ATP) were added, and then the reaction was carried out at 30° C. for 120 minutes.

Thereafter, in order to terminate and detect the reaction, 30 μl of the IMAP (registered trademark) binding reagent (IMAP Progressive Binding Reagent, R7284) that had been diluted (1:400) in the 1x IMAP binding buffer A (IMAP Progressive Binding Buffer A, 5x stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in dimethylsulfoxide (DMSO) was prepared, and then 0.5 μL of this solution was added for the testing to each well. Each control well was provided by adding 0.5 μL of DMSO to the well in place of the DMSO solution containing the compound to be tested.

Aurora B Inhibitory Activity (1) Measurement of Activity of Aurora B (Method A)

An assay development kit for IMAP (registered trademark) (Aurora B), purchased from Curia Biosciences, Inc., was used for phosphorylation reaction, and the phosphorylation of a substrate was detected using the IMAP technology. The assay development kit used is comprised of an assay buffer, GST-tagged human Aurora B(AurB)/His-tagged human INCENP complex proteins (amino acid sequence: 803-916, AAU04398.1), and an ATP/substrate solution. Using the same, the phosphorylation reaction was conducted in accordance with a partially revised protocol attached to the kit, and then the phosphorylation of the substrate was detected using the IMAP technology.

For the phosphorylation reaction, 384 well plate was used, and the reaction volume was 10 μl/well. The composition of the reaction buffer (assay buffer) is comprised of 20 mM of HEPES buffer (pH 7.4), 0.01% Tween-20, and 2 mM of dithiothreitol (DTT). Thereto, AurB/INCENP complex protein, 100 nM of the substrate, and 40 μM of ATP, and 1 mM of magnesium salt were added, and then the reaction was conducted at 25° C. for 45 minutes. Thereafter, in order to terminate and detect the reaction, 30 μl of the IMAP (registered trademark) binding reagent (IMAP Progressive Binding Reagent, R7284) that had been diluted (1:400) in the 1x IMAP binding buffer A (IMAP Progressive Binding Buffer A, 5x stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in DMSO was prepared, and then 0.5 μL of this solution was added for the testing to each well. Each control well was provided by adding 0.5 μL of DMSO to the well in place of the DMSO solution containing the compound to be tested.

(2) Measurement of activity of Aurora B (Method B)

(a) Purification of Aurora B cDNA of human Aurora B having histidine tag fused at the amino terminal was integrated into an expression vector, which was then highly expressed in *Escherichia coli* BL21-CodonPlus(DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(b) Measurement of Activity of Aurora B

For measurement of the activity of Aurora B, the substrate used was Kemptide (Leu-Arg-Arg-Ala-Ser-Leu-Gly) (SEQ.ID.NO.: 2), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 μL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetic acid (EDTA). To this, purified Aurora B, 100 μM of a substrate peptide, 100 μM of unlabeled adenosine triphosphate (ATP) and 1 μCi of [γ-$^{33}$P] labeled ATP (2,500 Ci/mmole or more) were added, and the mixture was reacted at 30° C. for 20 minutes. Then, 10 μL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 μL of this solution was added. A control was provided by adding 1.1 μL of DMSO to the reaction system.

Using the above method (in the measurement of activity of Aurora B, Method A was used), the results for measurement of the activities of Aurora A and Aurora B were obtained as shown in Table 1. The compound according to the invention exhibited excellent Aurora A selective inhibitory activity. Similar results are obtained when Method B is used in the measurement of activity of Aurora B.

TABLE 1

| Example | Inhibitory activity for Aurora A (IC50, nM) | Inhibitory activity for Aurora B (IC50, nM) |
| --- | --- | --- |
| Example 6 | 55 | >10000 |
| Example 8 | 9.1 | 7394 |
| Example 10 | 7.8 | 7906 |
| Example 13 | 1.1 | 6619 |
| Example 20 | 2.4 | 1153 |
| Example 21 | 0.81 | 275 |
| Example 23 | 4.0 | 2682 |
| Example 24 | <0.3 | 350 |

From the above, the compound according to the invention is believed to be useful as an antitumor agent since it exhibits excellent Aurora A selective inhibitory activity, leading to a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the Formula (I), the type of the compound represented by the Formula (I) used, and the dosage form of the compound represented by the Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated.

The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The therapeutic unit for sorafenib is such that, for example, 200 mg is orally administered twice a day (400 mg per day) at least 1 hour before or 2 hours after eating.

The therapeutic unit for sunitinib is such that, for example, 50 mg is orally administered once a day for four weeks, followed by 2 weels off.

Working Examples

In a thin-layer chromatography of Examples and Referential Examples, Silica gel 60 F254 (Merck) and Chromatolex NH (Fuji Silysia Chemical) was used as a plate and a UV detector was used in a detecting method. As pre-packed silica gel column for the chromatography, Biotage KP-Sil FLASH Cartridge (Biotage) or Purif-Pack Si (Moritex) were used. And KP-NH FLASH Cartridge (Biotage) or Purif-Pack NH (Moritex) was used for basic silica gel column chromatography. In a reversed phase preparative high performance liquid chromatography, XBridge Prep C18 (30×50 mm) (Waters) was used as a column, and a 0.1% aqueous trifluoroacetic acid solution and a 0.1% solution of trifluoroacetic acid in acetonitrile were used in a mobile phase. ESI-MS spectra were measured using micromass ZQ (Micromass). NMR spectra were measured using a spectrometer in a type of AL 400 (400 MHz; JEOL) and Inova 600 (600 MHz; Varian). For microwave reaction was used Initiator (Biotage).

Meanings of abbreviations used in the NMR measurement are as follows.

| | |
|---|---|
| s: | singlet |
| d: | doublet |

-continued

| | |
|---|---|
| dd: | double doublet |
| t: | triplet |
| dt: | double triplet |
| tt: | triple triplet |
| q: | quartet |
| m: | multiplet |
| br: | broad |
| brs: | broad singlet |
| Hz: | hertz |
| DMSO-$d_6$: | dimethylsulfoxide-$d_6$ |
| $CDCl_3$: | chloroform-d |
| $CD_3OD$: | methanol-$d_4$ |

Meanings of abbreviations used in experimental section are as follows.

| | |
|---|---|
| Boc : | tert-butoxycarbonyl group |
| dba : | dibenzylideneacetone |
| DIEA : | N,N-diisopropylethylamine |
| DMF : | N,N-dimethylformamide |
| DMSO: | dimethylsulfoxide |
| dppf : | 1,1'-bis(diphenylphosphino)ferrocene |
| EDCI : | N-[2-(dimethylamino)ethyl]-N'-ethylcarbodiimide |
| EtOAc : | ethyl acetate |
| HOBt : | 1H-benzotriazole |
| Me : | methyl group |
| MeOH : | methanol |
| Ms : | methanesulfonyl group |
| MsCl : | methanesulfonyl chloride |
| NMP : | N-methylpyrolidone |
| $PPh_3$ : | triphenylphosphine |
| RP-HPLC : | reverse phase high performance liquid chromatography |
| PTLC : | preparative thin layer chromatography |
| TEA : | triethylamine |
| TFA : | 2,2,2-trifluoroacetic acid |
| THF : | tetrahydrofuran |

EXAMPLE 1

Preparation of tert-butyl {(3R)-1-[4-methyl-6-(1H-pyrazol-5-ylamino)pyrimidin-2-yl]piperidin-3-yl}carbamate

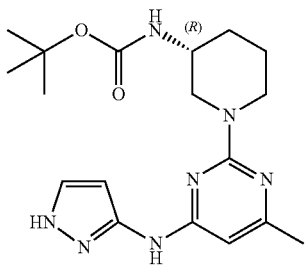

To the mixture of 2-chloro-6-methyl-N-(1H-pyrazol-5-yl)pyrimidin-4-amine prepared in Referential Example 1 (25.5 mg) and (R)-3-(tert-butoxycarbonylamino)piperidine (50.9 mg) in DMSO (5 ml) was added DIEA (210.0 μL). And the mixture was heated to 110° C. under stirring for overnight. The resulting mixture was cooled to room temperature, poured into brine and extracted with EtOAc. The extract was washed with saturated aqueous solution of $NaHCO_3$, dried over $Na_2SO_4$ and concentrated in vacuo. And the residue was purified with silica gel column chromatography (eluent: hexane/EtOAc=99/1~0/100) to give tert-butyl {(3R)-1-[4-methyl-6-(1H-pyrazol-5-ylamino)pyrimidin-2-yl]piperidin-3-yl}carbamate (26.0 mg) as a pale yellow solid.

ESI-MS m/z 374.5 $[M+H]^+$.

EXAMPLE 2

Preparation of tert-butyl {(3S)-1-[4-methyl-6-(1H-pyrazol-5-ylamino)pyrimidin-2-yl]piperidin-3-yl}carbamate

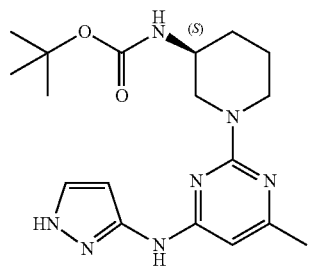

The title compound was prepared by the similar manner described in Example 1 using ethyl (R)-3-(tert-butoxycarbonylamino)piperidine instead of (S)-3-(tert-butoxycarbonylamino)piperidine:

ESI-MS m/z 374.5 $[M+H]^+$.

EXAMPLE 3

Preparation of (3S)-1-[4-methyl-6-(1H-pyrazol-5-ylamino)pyrimidine-2-yl]piperidine-3-carboxylic acid trifluoroacetate

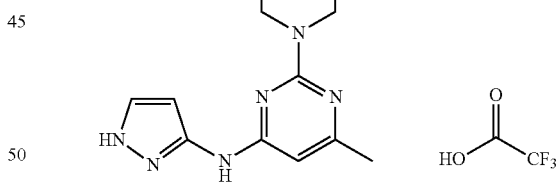

To the mixture of 2-chloro-6-methyl-N-(1H-pyrazol-5-yl)pyrimidin-4-amine prepared in Referential Example 1 (38.6 mg) and ethyl (S)-nipecotate (140.0 μL) in DMSO (3 ml) was added DIEA (250.0 μL). The mixture was heated to 100° C. under stirring overnight and then cooled to room temperature.

To the resulting mixture was added 1 M aqueous solution of NaOH (2 ml). The mixture was stirred at room temperature for 1 hour. 1 M aqueous solution of HCl (2 ml) was added to the resulting mixture for neutralization. And the mixture was concentrated to reduce solvents. The residue was purified with preparative RP-HPLC to give (3S)-1-[4-methyl-6-(1H-pyrazol-5-ylamino)pyrimidine-2-yl]piperidine-3-carboxylic acid trifluoroacetate (41.9 mg) as a pale yellow solid:

ESI-MS m/z 303.4 $[M+H]^+$.

EXAMPLE 4

Preparation of (3R)-1-[4-methyl-6-(1H-pyrazol-5-ylamino)pyrimidine-2-yl]piperidine-3-carboxylic acid trifluoroacetate

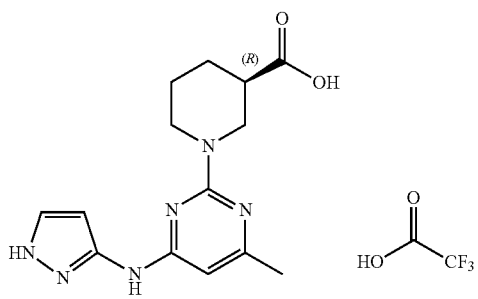

The title compound was prepared by the similar manner described in Example 3 using ethyl (R)-nipecotate instead of methyl (S)-nipecotate:

ESI-MS m/z 303.4 [M+H]$^+$.

EXAMPLE 5

Preparation of 6-methyl-2-(3-phenylpiperidine-1-yl)-N-(1H-pyrazol-5-yl)pyrimidin-4-amine trifluoroacetate

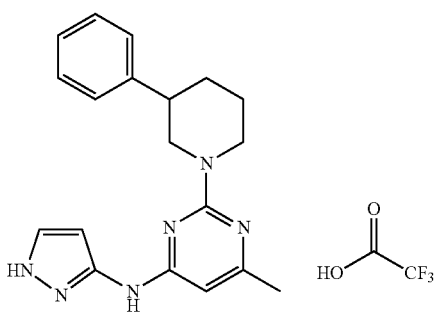

The title compound was prepared by the similar manner described in Example 1 using 3-phenylpiperidine instead of (R)-3-(tert-butoxycarbonylamino)piperidine. The purification of the crude product was performed with preparative RP-HPLC.

$^1$H NMR (400 MHz, CD$_3$OD) δ 1.74 (1H, tt), 1.80-2.00 (2H, m), 2.00-2.12 (1H, m), 2.34 (3H, s), 2.77-2.89 (1H, m), 3.07-3.28 (2H, m), 4.56 (2H, brs), 6.13 (1H, s), 6.50-6.95 (1H, m), 7.18-7.38 (5H, m), 7.46-7.71 (1H, m)

ESI-MS m/z 335.2 [M+H]$^+$.

EXAMPLE 6

Preparation of trans-5-[(tert-butoxycarbonyl)amino]-1-[4-methyl-6-(1H-pyrazol-5-ylamino)pyrimidin-2-yl]piperidine-3-carboxylic acid

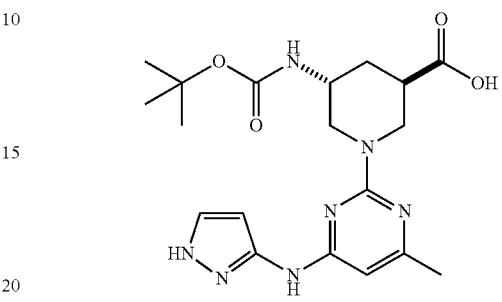

Step 1: Preparation of 1-tert-butyl 3-methyl trans-5-hydroxypiperidine-1,3-dicarboxylate

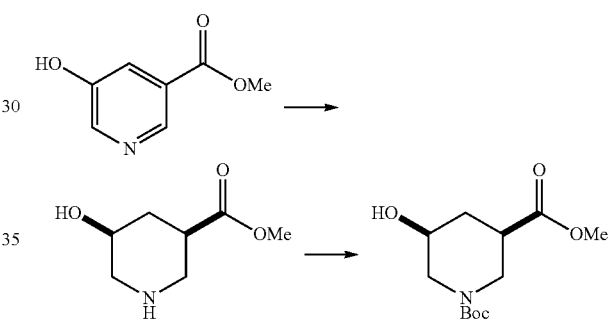

A solution of methyl 5-hydroxynicotinate (1.50 g) in MeOH (30 ml) was hydrogenated (ca. 4 atm) for 3 days in a Parr low-pressure hydrogenation apparatus with a 5 wt. % Rh on Al$_2$O$_3$ catalyst (300 mg) at 70° C. Rh on Al$_2$O$_3$ catalyst was filtered off and the filtrate was concentrated in vacuo to give the crude methyl cis-5-hydroxypiperidine-3-carboxylate as a pale yellow oil.

The crude 3,5-cis-cordinated piperidine was dissolved into dioxane (30 ml). To the solution was added di-tert-butyl Bicarbonate (3 ml) and TEA (3 ml) at room temperature. After 2 hours stirring at room temperature, the mixture was concentrated in vacuo. And the residue was purified with silica gel column chromatography (eluent: CHCl$_3$/MeOH=100/0~90/10) to give 1-tert-butyl 3-methyl trans-5-hydroxypiperidine-1,3-dicarboxylate as a pale yellow oil.

Step 2: Preparation of 1-tert-butyl 3-methyl trans-5-azidopiperidine-1,3-dicarboxylate

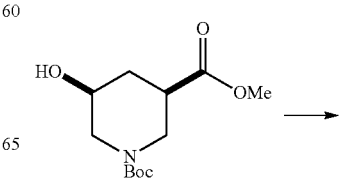

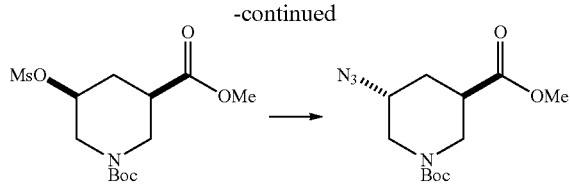

To the solution of 1-tert-butyl 3-methyl trans-5-hydroxypiperidine-1,3-dicarboxylate in CHCl₃ (2 ml) was added DIEA (2 ml) and MsCl (500 μl) at room temperature. And the mixture was stirred at room temperature for 1 hour. After the period, the mixture was poured into saturated aqueous solution of NaHCO₃ and extracted with CHCl₃. The extract was dried over Na₂SO₄ and concentrated to give the crude 1-tert-butyl 3-methyl-cis-5-[(methylsulfonyl)oxy]piperidine-1,3-dicarboxylate as a pale brown oil.

The crude mesylate was dissolved into DMF (20 ml). To the solution was added NaN₃ (953.5 mg) and the mixture was heated to 80° C. under stirring overnight. The mixture was poured into saturated aqueous solution of NaHCO₃ and extracted with CHCl₃. The extract was dried over Na₂SO₄ and concentrated. The residue was purified with silica gel column chromatography (eluent: hexane/EtOAc=93/7~50/50) to give 1-tert-butyl 3-methyl trans-5-azidopiperidine-1,3-dicarboxylate (343.0 mg) as a pale yellow oil.

¹H NMR (400 MHz, CDCl₃) δ 1.47 (9H, s), 1.86-2.22 (2H, m), 2.80 (1H, m), 2.93-3.53 (2H, m), 3.69 (3H, s), 3.80-4.08 (1H, m), 3.85 (1H, s), 4.08-4.35 (1H, m)

ESI-MS m/z 285.1 [M+H]⁺.

Step 3: Preparation of methyl trans-5-azido-1-[4-methyl-6-(1H-pyrazol-5-ylamino)pyrimidin-2-yl]piparidine-3-carboxylate

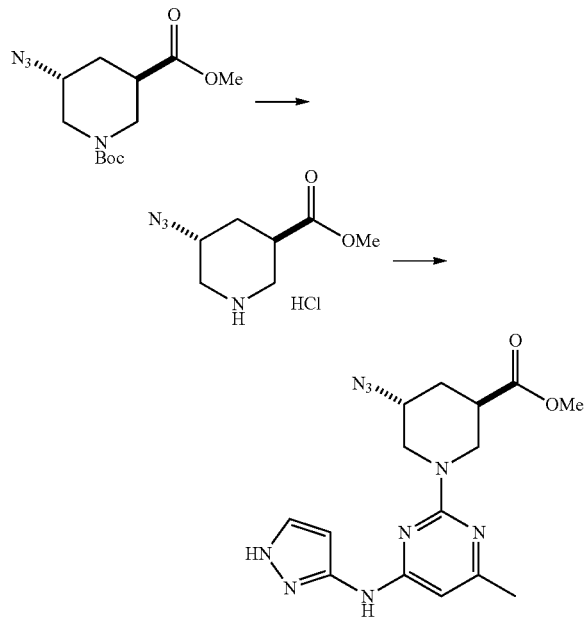

To the solution of 1-tert-butyl 3-methyl trans-5-azidopiperidine-1,3-dicarboxylate (343.0 mg) in MeOH (1 ml) was added 10% solution of HCl in MeOH (15 ml). After stirring for 30 minutes at room temperature, the mixture was concentrated to give the crude methyl cis-5-azidopiperidine-3-carboxylate hydrochloride (120.3 mg) as a pale brown solid.

The crude piperidine hydrochloride was dissolved into DMSO (7 ml). To the solution was added 2-chloro-6-methyl-N-(1H-pyrazol-5-yl)pyrimidin-4-amine prepared in Referential Example 1 (96.0 mg) and DIEA (0.50 ml). And the mixture was stirred at 110° C. for 12 hours. The mixture was cooled to room temperature, poured into saturated aqueous solution of NaHCO₃ and extracted with CHCl₃. The extract was washed with brine, dried over Na₂SO₄ and concentrated in vacua. The residue was purified with silica gel column chromatography (eluent: CHCl₃/MeOH=98/2~85/15) to give methyl trans-5-azido-1-[4-methyl-6-(1H-pyrazol-5-ylamino)pyrimidin-2-yl]piparidine-3-carboxylate (13.5 mg) as pale yellow solid.

¹H NMR (400 MHz, CDCl₃) δ 1.99-2.14 (2H, m), 2.25 (3H, s), 2.90 (1H, m), 3.56-3.75 (2H, m), 3.69 (3H, s), 3.93 (1H, m), 4.29 (1H, dd), 4.42-4.53 (2H, m), 6.09 (1H, s), 6.31 (1H, s), 7.20 (1H, brs), 7.49 (1H, d)

ESI-MS m/z 358.1 [M+H]⁺.

Step 4: Preparation of methyl cis-5-amino-1-[4-methyl-6-(1H-pyrazol-5-ylamino)pyrimidin-2-yl]piperidine-3-carboxylate

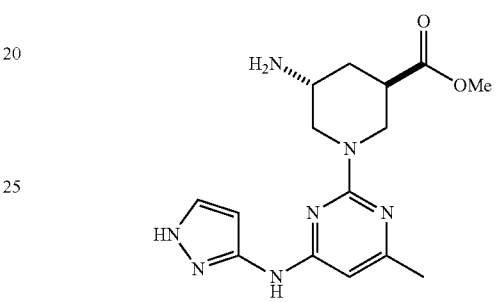

To the solution of methyl trans-5-azido-1-[4-methyl-6-(1H-pyrazol-5-ylamino)pyrimidin-2-yl]piparidine-3-carboxylate (13.5 mg) in the mixed solvent of THF (4 ml) and water (2 ml) was added PPh₃ (22.5 mg) at room temperature. And the mixture was refluxed for 6 hours. The reaction mixture was concentrated in vacuo to give the crude methyl cis-5-amino-1-[4-methyl-6-(1H-pyrazol-5-ylamino)pyrimidin-2-yl]piperidine-3carboxylate as a pale yellow amorphous form.

Step 5: Preparation of trans-5-[(tert-butoxycarbonyl)amino]-1-[4-methyl-6-(1H-pyrazol-5-ylamino)pyrimidin-2-yl]piperidine-3-carboxylic acid

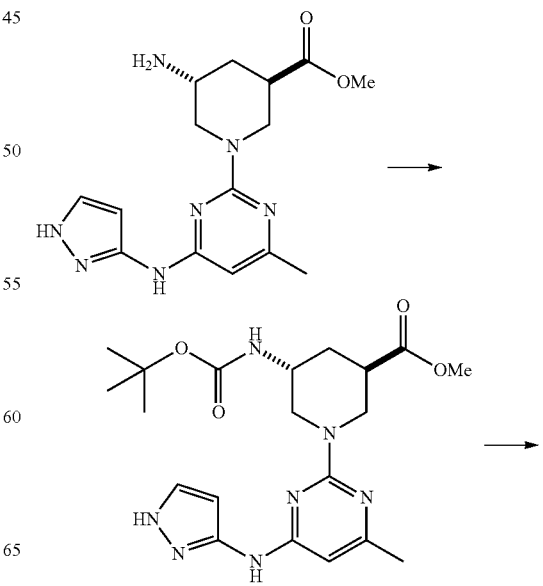

-continued

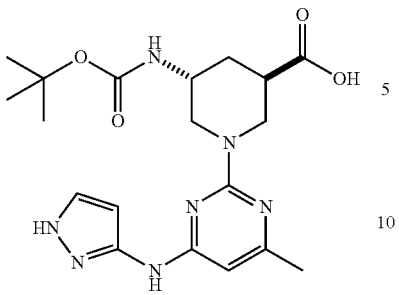

To the solution of the crude methyl cis-5-amino-1-[4-methyl-6-(1H-pyrazol-5-ylamino)pyrimidin-2-yl]piperidine-3-carboxylate in CHCl₃ (6 ml) was added di-tert-butyl dicarbamate (20 μl) and DIEA (100 μl) at room temperature. After stirring for 1 hour, the mixture was concentrated in vacua to give the crude methyl cis-5-[(tert-butoxycarbonyl)amino]-1-[4-methyl-6-(1H-pyrazol-5-ylamino)pyrimidin-2-yl]piperidine-3-carboxylate as a pale yellow solid.

The crude carbamate was dissolved into MeOH (4 ml). 2 M aqueous solution of NaOH was added at room temperature. And the mixture was stirred at room temperature for 4 hours. After the addition of NH₄Cl for neutralization, the resulting reaction mixture was concentrated in vacuo. The residue was suspended into the mixed solvent of CHCl₃/MeOH. The insoluble material was filtered off and the filtrate was concentrated again. The residue was purified with silica gel PTLC (eluent: CHCl₃/MeOH=6/1) to give trans-5-[(tert-butoxycarbonyl)amino]-1-[4-methyl-6-(1H-pyrazol-5-ylamino)pyrimidin-2-yl]piperidine-3-carboxylic acid (10.9 mg) as colorless solid.

¹H NMR (400 MHz, CD₃OD) δ 1.22-1.50 (1H, m), 1.39 (9H, s), 1.86-2.03 (1H, m), 2.03-2.20 (1H, m), 2.26 (3H, s), 2.65-2.86 (1H, m), 3.60-3.88 (2H, m), 3.88-4.07 (1H, m), 4.07-4.22 (1H, m), 6.17 (1H, s), 6.51 (1H, s), 7.53 (1H, s)

ESI-MS m/z 418.4 [M+H]⁺.

EXAMPLE 7

Preparation of trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid trifluoroacetate

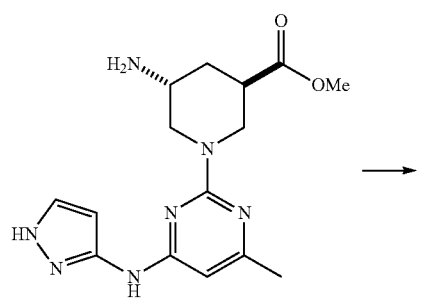

-continued

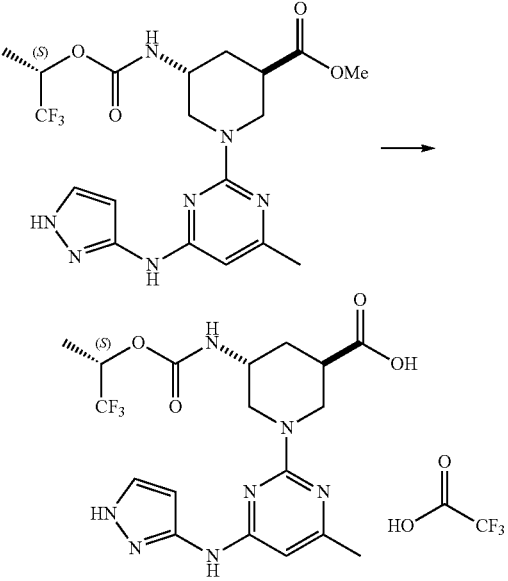

The crude methyl cis-5-amino-1-[4-methyl-6-(1H-pyrazol-5-ylamino)pyrimidin-2-yl]piperidine-3-carboxylate prepared in Step 4 of Example 6 was dissolved into CHCl₃ (6 ml). To the solution was added the solution of 4-nitrophenyl (2S)-1,1,1-trifluoropropan-2-yl carbonate (203.3 mg) in CHCl₃ and DIEA (125.0 μl). After stirring at room temperature for 2 hours, the mixture was concentrated in vacuo. The residue was dissolved into EtOAc, poured into 1 M aqueous solution of NaOH and extracted with EtOAc. The extract was washed with saturated aqueous solution of NaHCO₃, dried over MgSO₄ and concentrated to give the crude methyl cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylate as a pale orange amorphous form.

To the solution of the crude carbamate in the mixed solvent of THF (1 ml) and MeOH (6 ml) was added 1 M aqueous solution of NaOH (1 ml). And the mixture was stirred at room temperature for 4 hours. After the addition of excess amount of NH₄Cl, the mixture was concentrated. The residue was purified with preparative RP-HPLC to give trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid trifluoroacetate (48.0 mg) as pale orange solid.

¹H NMR (400 MHz, CD₃OD) δ 1.29 and 1.37 (3H, d), 1.93-2.07 (1H, m), 2.19-2.34 m), 2.36 and 2.37 (3H, s), 2.93-3.05 (1H, m), 3.60-4.22 (5H, m), 5.16-5.32 (1H, in), 6.00-6.95 (2H, br), 7.57 and 7.61 (1H, s)

ESI-MS m/z 458.3 [M+H]⁺.

EXAMPLE 8

Preparation of cis-5-[(tert-butoxycarbonyl)amino]-1-[4-methyl-6-(1H-pyrazol-5-ylamino)pyrimidin-2-yl]piperidine-3-carboxylic acid

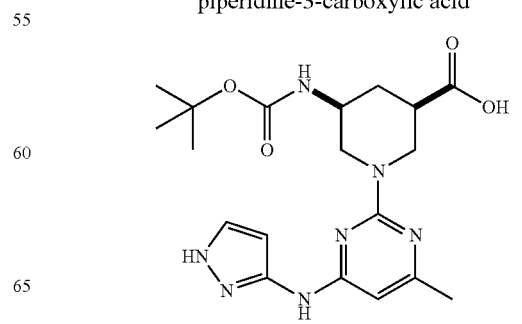

Step 1: Preparation of methyl 5-aminopyridine-3-carboxylate

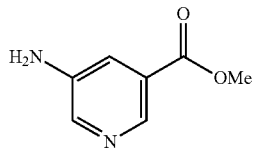 [SMILES: COC(=O)c1cncc(N)c1]

3-Aminonicotinic acid (691.1 mg) was suspended into the mixed solvent of toluene (20 ml) and MeOH (10 ml). To the suspension was added 0.6 M solution of trimethylsilyldiazometane in hexane (12 ml) at room temperature. After stirring for 2 hours, the mixture was concentrated in vacuo. The residue was suspended into hexane and the precipitate was collected by filtration. The collected solid was purified with silica gel column chromatography (eluent: CHCl3/MeOH=99/1~88/12) to give methyl 5-aminopyridine-3-carboxylate (700.0 mg) as a pale orange solid.

$^1$H NMR (400 MHz, CDCl$_3$) δ 3.93 (3H, s), 7.56 (1H, dd), 8.24 (1H, dd), 8.62 (1H, dd)

ESI-MS m/z 153.2 [M+H]$^+$.

Step 2: Preparation of methyl cis-5-aminopiperidine-3-carboxylate dihydrochloride

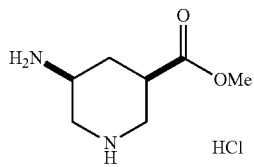 [SMILES: COC(=O)[C@H]1CNC[C@@H](N)C1 ; Cl]

To the solution of methyl 5-aminopyridine-3-carboxylate (700.0 mg) in MeOH (20 ml) was added 2 M aqueous solution of HCl (7 ml). And the mixture was hydrogenated (ca. 4 atm) for 1 day in a Parr low-pressure hydrogenation apparatus with a 5 wt. % Rh on Al$_2$O$_3$ catalyst (451.9 mg) at 80° C. Rh on Al$_2$O$_3$ catalyst was filtered off and the filtrate was concentrated in vacuo. The residue was solidified from the mixed solvent of CHCl$_3$ and MeOH to give methyl cis-5-aminopiperidine-3-carboxylate dihydrochloride as a cream-colored solid.

$^1$H NMR (400 MHz, CD$_3$OD) δ 2.49-2.60 (1H, m), 2.90-3.75 (7H, m), 3.75 (3H, s).

Step 3: Preparation of methyl cis-5-[(tert-butoxycarbonyl)amino]-1-[4-methyl-6-(1H-pyrazol-5-ylamino)pyrimidin-2-yl]piparidine-3-carboxylate

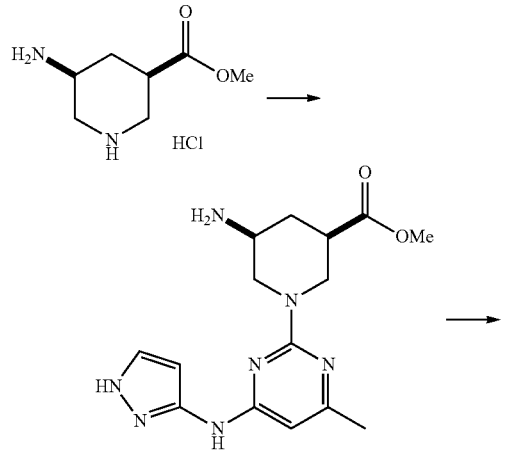

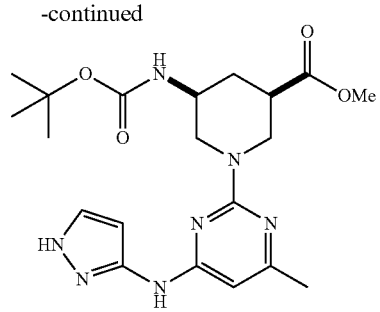

To the solution of methyl cis-5-aminopiperidine-3-carboxylate dihydrochloride (140.0 mg) in DMSO (10 ml) was added 2-chloro-6-methyl-N-(1H-pyrazol-5-yl)pyrimidin-4-amine prepared in Referential Example 1 (69.7 mg) and DIEA (0.57 ml). And the mixture was stirred at 130° C. overnight and cooled to room temperature.

To the resulting mixture was added di-tert-butyl dicarbamate (165.0 μl) at room temperature. After stirring for 2 hours, the mixture was poured into saturated aqueous solution of NaHCO$_3$ and extracted with EtOAc. The extract was washed with brine, dried over Na$_2$SO$_4$ and concentrated in vacuo. The residue was purified with basic silica gel column chromatography (eluent: CHCl$_3$/MeOH=100/0~93/7) to give methyl cis-5-[(tert-butoxycarbonyl)amino]-1-[4-methyl-6-(1H-pyrazol-5-ylamino)pyrimidin-2-yl]piperidine-3-carboxylate (12.6 mg) as pale yellow solid.

$^1$H NMR (400 MHz, CDCl$_3$) δ 1.46 (9H, s), 1.63 (1H, q), 2.23 (3H, s), 2.26-2.40 (1H, m), 2.60-2.70 (1H, m), 2.81 (1H, t), 3.12 (1H, t), 3.58-3.77 (1H, m), 3.72 (3H, s), 4.68-4.85 (3H, m), 6.07 (1H, s), 6.33 (1H, s), 7.45 (1H, d), 7.48 (1H, s)

ESI-MS in/z 432.5 [M+H]$^+$.

Step 4: Preparation of cis-5-[(tert-butoxycarbonyl)amino]-1-[4-methyl-6-(1H-pyrazol-5-ylamino)pyrimidin-2-yl]piperidine-3-carboxylic acid

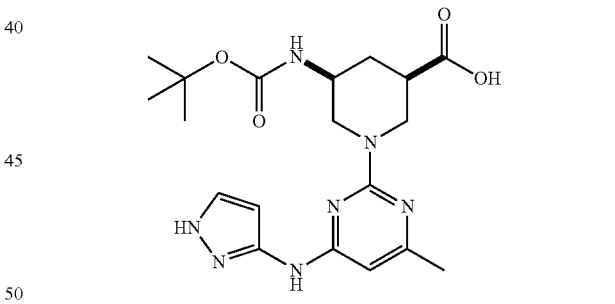

To the solution of methyl cis-5-[(tert-butoxycarbonyl)amino]-1-[4-methyl-6-(1H-pyrazol-5-ylamino)pyridin-2-yl]piperidine-3-carboxylate (11.0 mg) in MeOH (5 ml) was added 5 M aqueous solution of NaOH (468.0 μl) at room temperature. After stirring for 4 hours, NH$_4$Cl was added for neutralization and the mixture was concentrated. The residue was suspended into the mixed solvent of CHCl$_3$ and MeOH. The insoluble material was removed by filtration. The filtrate was concentrated and the residue was purified with preparative RP-HPLC. The desired fraction was neutralized by addition of aqueous solution of NH$_3$ and concentrated. And the residue was purified again with preparative RP-HPLC (mobile phase: H$_2$O and acetonitlile, without TFA) to give cis-5-[(tert-butoxycarbonyl)amino]-1-[4-methyl-6-(1H-pyrazol-5-ylamino)pyridin-2-yl]piperidine-3-carboxylic acid (1.82 mg) as colorless solid.

$^1$H NMR (400 MHz, DMSO-d$_6$) δ 1.45 (9H, s), 1.67 (1H, q), 2.27-2.38 (1H, m), 2.35 (3H, s), 2.62-2.73 (1H, m), 2.87 (1H, dd), 3.11 (1H, dd), 3.52-3.64 (1H, m), 4.56-4.64 (1H, m), 4.64-4.76 (1H, m), 6.25-6.46 (1H, br), 6.46-6.64 (1H, br), 7.56 (1H, d)

ESI-MS m/z 418.5 [M+H]$^+$.

EXAMPLE 9

Preparation of methyl cis-1-[4-methyl-6-(1H-pyrazol-5-ylamino)pyrimidin-2-yl]-5-phenylpiperidine-3-carboxylate trifluoroacetate

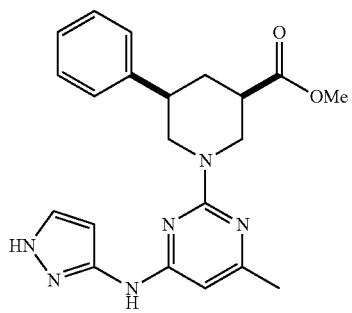 [SMILES: COC(=O)[C@@H]1C[C@H](c2ccccc2)CN(c2nc(C)cc(Nc3cc[nH]n3)n2)C1]

The title compound was prepared by the similar manner described in Example 1 using methyl cis-5-phenylpiperidine-3-carboxylate (its synthetic procedure is described in *Bioorg. Med. Chem.*, 2008, 16, 3816-3824) instead of (S)-3-(tert-butoxycarbonylamino)piperidine. The purification of the crude product was performed with preparative RP-HPLC.

$^1$H NMR (400 MHz, CD$_3$OD) δ 1.91-2.10 (1H, m), 2.30-2.43 (1H, m), 2.37 (3H, s), 2.80-2.99 (2H, m), 3.10-3.35 (2H, m), 3.74 (3H, s), 4.42-4.73 (1H, br), 4.73-5.20 (1H, br), 6.02-6.30 (1H, br), 6.50-7.02 (1H, m), 7.21-7.77 (7H, m)

ESI-MS m/z 379.2 [M+H]$^+$.

EXAMPLE 10

Preparation of cis-1-[4-methyl-6-(1H-pyrazol-5-ylamino)pyrimidin-2-yl]-5-phenylpiperidine-3-carboxylic acid trifluoroacetate

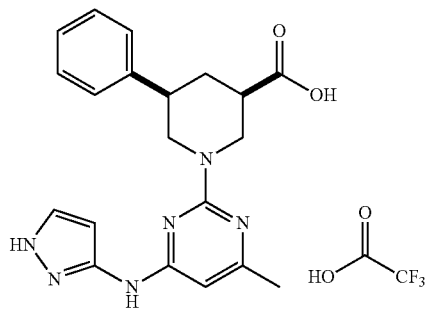

To the solution of methyl cis-1-[4-methyl-6-(1H-pyrazol-5-ylamino)pyrimidin-2-yl]-5-phenylpiperidine-3-carboxylate trifluoroacetate (34.9 mg) in MeOH (3 ml) was added 2 M aqueous solution of NaOH (1 ml). And the mixture was stirred at room temperature for 1 hour. The mixture was concentrated followed by addition of TFA for neutralization. The residue was purified with preparative RP-HPLC to give cis-1-[4-methyl-6-(1H-pyrazol-5-ylamino)pyrimidin-2-yl]-5-phenylpiperidine-3-carboxylic acid trifluoroacetate (34.9 mg) as a colorless solid.

$^1$H NMR (400 MHz, CD$_3$OD) δ 1.90-2.10 (1H, m), 2.28-2.48 (1H, m), 2.37 (3H, s), 2.73-2.88 (1H, m), 2.88-3.00 (1H, m), 3.10-3.37 (2H, m), 4.44-4.75 (1H, br), 6.05-6.31 (1H, br), 6.50-7.02 (1H, m), 7.22-7.43 (5H, m), 7.47-7.73 (1H, m)

ESI-MS m/z 379.2 [M+H]$^+$.

EXAMPLE 11

Preparation of cis-1-[4-methyl-6-(1H-pyrazol-5-ylamino)pyrimidin-2-yl]-5-[3-(trifluoromethyl)phenyl]piperidine-3-carboxylic acid trifluoroacetate

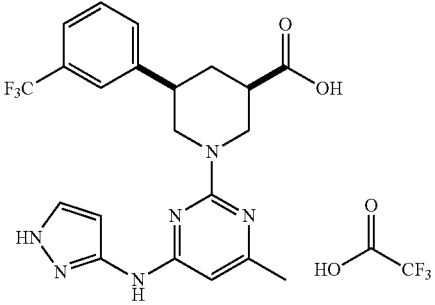

Step 1: Preparation of methyl 5-[3-(trifluoromethyl)phenyl]nicotinate

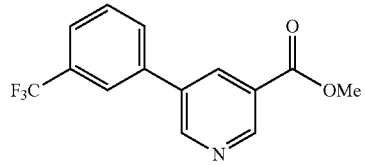 [SMILES: COC(=O)c1cncc(-c2cccc(C(F)(F)F)c2)c1]

Methyl 5-bromonicotinate (168.2 mg), 3-trifluoromethyl-benzeneboronic acid (165.6 mg), K$_3$PO$_4$ (378.5 mg) and Pd(PPh$_3$)$_4$ (92.2 mg) was mixed in dioxane (5 ml). To the suspension was added water (0.25 ml). And the mixture was heated to 100° C. under stirring. After 6 hours, the mixture was cooled to room temperature and was diluted with EtOAc. The insoluble material was filtered off and washed with EtOAc. The filtrate was poured into saturated aqueous solution of NaHCO$_3$ and extracted with EtOAc. The extract was washed with brine, dried over MgSO$_4$ and concentrated. The residue was purified with silica gel column chromatography (eluent: hexane/EtOAc=94/6~50/50) to give methyl 5-[3-(trifluoromethyl)phenyl]nicotinate (190.1 mg) as a pale yellow solid.

$^1$H NMR (400 MHz, CDCl$_3$) δ 4.01 (3H, s), 7.65 (1H, t), 7.71 (1H, d), 7.81 (1H, d), 7.87 (1H, s), 8.51 (1H, t), 9.02 (1H, d), 9.25 (1H, d)

ESI-MS m/z 282.1 [M+H]$^+$.

Step 2: Preparation of methyl cis-5-[3-(trifluoromethyl)phenyl]piperidine-3-carboxylate

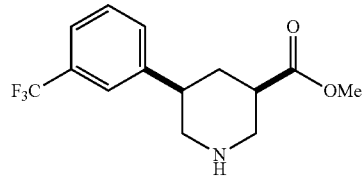 [SMILES: COC(=O)[C@H]1CNC[C@@H](c2cccc(C(F)(F)F)c2)C1]

A solution of methyl 5-[3-(trifluoromethyl)phenyl]nicotinate (190.1 mg) in MeOH (30 ml) was hydrogenated (ca. 4 atm) for 2 days in a Parr low-pressure hydrogenation apparatus with a 5 wt. % Rh on $Al_2O_3$ catalyst (121.6 mg) at 90° C. Rh on $Al_2O_3$ catalyst was filtered off and the filtrate was concentrated in vacuo. The residue was purified with silica gel column chromatography (eluent: CHCl3/MeOH=98/2~90/10) to give methyl cis-5-[3-(trifluoromethyl)phenyl]piperidine-3-carboxylate (71.2 mg) as a pale brown oil.

$^1$H NMR (400 MHz, $CDCl_3$) δ 1.82 (1H, q), 1.88 (1H, s), 2.27-2.33 (1H, m), 2.60-2.83 (4H, m), 3.15-3.22 (1H, m), 3.37-3.43 (1H, m), 3.69 (3H, s), 7.38-7.51 m)

ESI-MS m/z 288.2 $[M+H]^+$.

Step 3: Preparation of cis-1-[4-methyl-6-(1H-pyrazol-5-ylamino)pyrimidin-2-yl]-5-[3-(trifluoromethyl)phenyl]piperidine-3-carboxylic acid trifluoroacetate

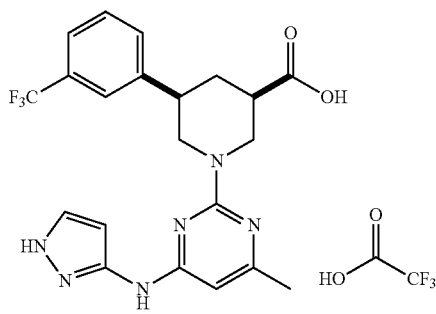

The title compound was prepared by the similar manner described in Example 1 using methyl cis-5-[3-(trifluoromethyl)phenyl]piperidine-3-carboxylate prepared in Step 3 of Example 1 instead of (S)-3-(cert-butoxycarbonylamino)piperidine, followed by the hydrolysis by a similar manner to Example 10.

$^1$H NMR (400 MHz, $CD_3OD$) δ 1.92-2.14 (1H, m), 2.29-2.55 m), 2.37 (3H, s), 2.76-2.92 (1H, m), 2.98-3.15 (1H, m), 3.15-3.38 (2H, m), 4.38-5.25 (2H, m), 6.04-6.33 (1H, m), 6.50-7.05 (1H, m), 7.44-7.74 (5H, m)

ESI-MS m/z 447.4 $[M+H]^+$.

EXAMPLE 12

Preparation of methyl cis-5-cyclohexyl-1-[4-methyl-6-(1H-pyrazol-5-ylamino)pyrimidin-2-yl]piperidine-3-carboxylate trifluoroacetate

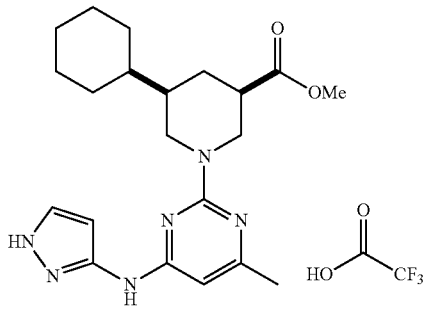

The title compound was prepared by the similar manner described in Example 1 using methyl cis-5-cyclohexylpiperidine-3-carboxylate (its synthetic procedure is described in *Bioorg. Med. Chem.*, 2008, 16, 3816-3824) instead of (S)-3-(tert-butoxycarbonylamino)piperidine. The purification of the crude product was performed with preparative RP-HPLC.

$^1$H NMR (400 MHz, $CD_3OD$) δ 0.95-1.36 (7H, m), 1.36-1.54 (2H, m), 1.55-1.87 (5H, m), 2.18-2.32 (1H, m), 2.37 (3H, s), 2.57-2.72 (1H, m), 2.72-2.86 (1H, m), 2.99-3.20 (1H, m), 3.73 (3H, s), 4.40-4.90 (2H, br), 6.14 (1H, s), 6.58-6.98 (1H, m), 7.63 (1H, s)

ESI-MS m/z 399.2 $[M+H]^+$.

EXAMPLE 13

Preparation of cis-5-cyclohexyl-1-[4-methyl-6-(1H-pyrazol-5-ylamino)pyrimidin-2-yl]piperidine-3-carboxylic acid trifluoroacetate

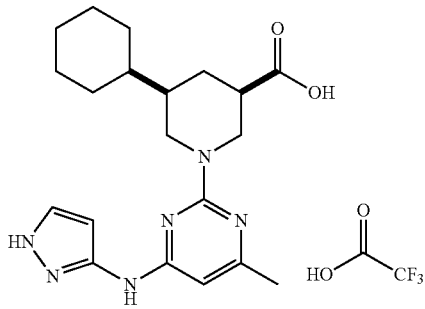

The title compound was prepared by the similar manner described in Example 10 using methyl cis-5-cyclohexyl-1-[4-methyl-6-(1H-pyrazol-5-ylamino)pyrimidin-2-yl]piperidine-3-carboxylate trifluoroacetate prepared in Example 12 instead of methyl cis-1-[4-methyl-6-(1H-pyrazol-5-ylamino)pyrimidin-2-yl]-5-phenylpiperidine-3-carboxylate trifluoroacetate. The purification of the crude product was performed with preparative RP-HPLC.

$^1$H NMR (400 MHz, $CD_3OD$) δ 0.96-1.37 (6H, m), 1.37-1.54 (2H, m), 1.58-1.90 (6H, m), 2.18-2.34 (1H, m), 2.36 (3H, s), 2.51-2.69 (1H, m), 2.70-2.90 (1H, m), 2.99-3.20 (1H, m), 4.35-4.90 (2H, m), 6.14 (1H, s), 6.57-6.99 (1H, m), 7.61 (1H, s)

ESI-MS m/z 385.2 [M+H]⁺.

EXAMPLE 14

Preparation of cis-5-cyclohexyl-1-[4-methyl-6-(1,3-thiazol-2-ylamino)pyrimidin-2-yl]piperidine-3-carboxylic acid trifluoroacetate

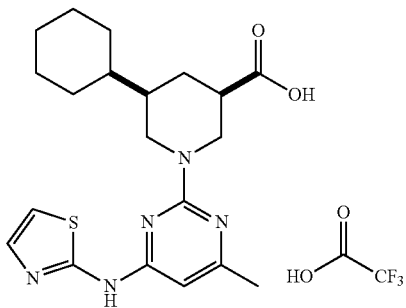

The title compound was prepared by the similar manner described in Example 1 and Example 10. Methyl cis-5-cyclohexylpiperidine-3-carboxylate was used instead of (S)-3-(tert-butoxycarbonylamino)piperidine, and 2-chloro-6-methyl-N-(1,3-thiazol-2-yl)pyrimidin-4-amine prepared in Referential Example 3 was used instead of 2-chloro-6-methyl-N-(1H-pyrazol-5-yl)pyrimidin-4-amine in Example 1.

¹H NMR (400 MHz, CD₃OD) δ 1.00-1.39 (6H, m), 1.39-1.60 (2H, m), 1.60-1.90 (5H, m), 2.22-2.35 (1H, m), 2.41 (3H, s), 2.63 (1H, tt), 2.82-2.97 (1H, m), 3.04-3.23 (1H, m), 4.00-5.70 (2H, br), 6.27 (1H, s), 7.23 (1H, d), 7.52 (1H, d)

ESI-MS m/z 402.4 [M+H]⁺.

EXAMPLE 15

Preparation of cis-1-{4-[(5-cyano-1,3-thiazol-2-yl)amino]-6-methylpyrimidin-2-yl}-5-cyclohexylpiperidine-3-carboxylic acid trifluoroacetate

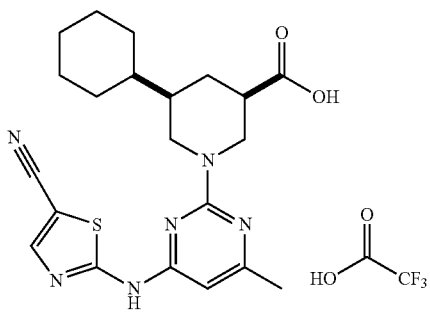

The title compound was prepared by the similar manner described in Example 1 and Example 10. Methyl cis-5-cyclohexylpiperidine-3-carboxylate was used instead of (5)-3-(tert-butoxycarbonylamino)piperidine, and 2-[(2-chloro-6-methylpyrimidin-4-yl)amino]-1,3-thiazole-5-carbonitrile prepared in Referential Example 5 was used instead of 2-chloro-6-methyl-N-(1H-pyrazol-5-yl)pyrimidin-4-amine in Example 1.

¹H NMR (400 MHz, CD₃OD) δ 1.04-1.42 (6H, m), 1.42-1.64 (2H, m), 1.64-1.74 (1H, m), 1.74-2.03 (4H, m), 2.25-2.41 (1H, m), 2.47 (3H, s), 2.69 (1H, tt), 2.83-3.06 (1H, m), 3.13-3.28 (1H, m), 4.15-5.30 (2H, br), 6.35 (1H, s), 8.16 (1H, s)

ESI-MS m/z 427.4 [M+H]⁺.

EXAMPLE 16

Preparation of cis-5-cyclohexyl-1-{4-[(5-cyclopropyl-1,3-thiazol-2-yl)amino]-6-methylpyrimidin-2-yl}piperidine-3-carboxylic acid trifluoroacetate

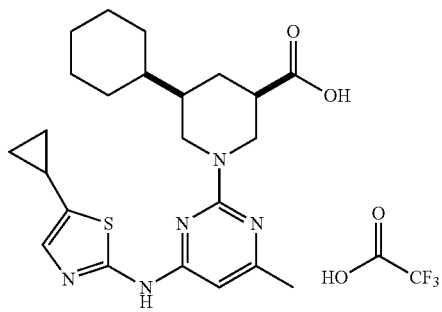

The title compound was prepared by the similar manner described in Example 1 and Example 10. Methyl cis-5-cyclohexylpiperidine-3-carboxylate was used instead of (S)-3-(tert-butoxycarbonylamino)piperidine, and 2-chloro-N-(5-cyclopropyl-1,3-thiazol-2-yl)-6-methylpyrimidin-4-amine prepared in Referential Example 4 was used instead of 2-chloro-6-methyl-N-(1H-pyrazol-5-yl)pyrimidin-4-amine in Example 1.

¹H NMR (400 MHz, CD₃OD) δ 0.63-0.79 (2H, m), 0.93-1.07 (2H, m), 1.07-1.41 (6H, m), 1.41-1.61 (2H, in), 1.61-1.94 (5H, m), 1.94-2.06 (1H, m), 2.20-2.37 (1H, m), 2.40 (3H, s), 2.57-2.71 (1H, m), 2.78-3.02 (1H, m), 3.02-3.23 (1H, m), 3.80-5.60 (2H, br), 6.23 (1H, s), 7.14-7.23 (1H, m)

ESI-MS m/z 442.5 [M+H]⁺.

EXAMPLE 17

Preparation of cis-5-cyclohexyl-1-{4-[(3-cyclopropyl-1H-pyrazol-5-yl)amino]-6-methylpyrimidin-2-yl}piperidine-3-carboxylic acid

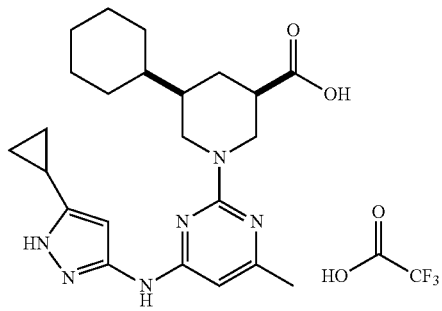

Step 1: Preparation of methyl cis-5-cyclohexyl-1-{4-[(3-cyclopropyl-1H-pyrazol-5-yl)amino]-6-methylpyrimidin-2-yl}piperidine-3-carboxylate

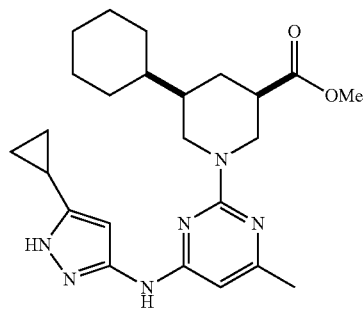 [SMILES: COC(=O)[C@@H]1C[C@H](C2CCCCC2)CN(c2nc(C)cc(Nc3cc(C4CC4)[nH]n3)n2)C1]

The title compound was prepared by the similar manner described in Example 1 using methyl cis-5-cyclohexylpiperidine-3-carboxylate instead of (S)-3-(tert-butoxycarbonylamino)piperidine, and 2-chloro-N-(3-cyclopropyl-1H-pyrazol-5-yl)-6-methylpyrimidin-4-amine prepared in Referential Example 2 instead of 2-chloro-6-methyl-N-(1H-pyrazol-5-yl)pyrimidin-4-amine.

ESI-MS m/z 439.4 [M+H]⁺.

Step 2: Preparation of cis-5-cyclohexyl-1-{4-[(3-cyclopropyl-1H-pyrazol-5-yl)amino]-6-methylpyrimidin-2-yl}piperidine-3-carboxylic acid trifluoroacetate

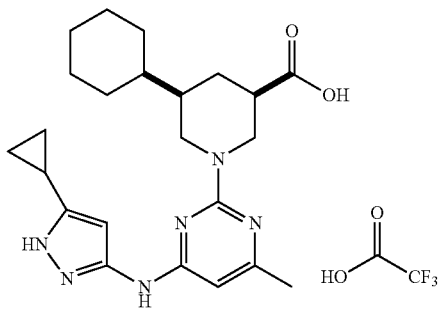

The title compound was prepared by the similar manner described in Example 10 using methyl cis-5-cyclohexyl-1-{4-[(3-cyclopropyl-1H-pyrazol-5-yl)amino]-6-methylpyrimidin-2-yl}piperidine-3-carboxylate prepared in Step 1 instead of methyl cis-1-[4-methyl-6-(1H-pyrazol-5-ylamino)pyrimidin-2-yl]-5-phenylpiperidine-3-carboxylate trifluoroacetate.

¹H NMR (400 MHz, CD₃OD) δ 0.70-0.78 (2H, m), 0.96-1.03 (2H, m), 1.03-1.38 (7H, m), 1.38-1.54 (2H, m), 1.63-1.73 (1H, m), 1.73-1.86 (4H, m), 1.86-1.94 (1H, m), 2.22-2.32 (1H, m), 2.35 (3H, s), 2.53-2.66 (1H, m), 2.71-2.89 (1H, m), 3.00-3.18 (1H, m), 4.32-4.90 (2H, br), 6.11 (1H, brs), 6.30 (1H, brs)

ESI-MS m/z 425.5 [M+H]⁺.

EXAMPLE 18

Preparation of methyl (3S*,5S*)-5-cyclohexyl-1-{4-[(3-cyclopropyl-1H-pyrazol-5-yl)amino]-6-methylpyrimidin-2-yl}piperidine-3-carboxylate

EXAMPLE 19

Preparation of methyl (3R*,5R*)-5-cyclohexyl-1-{4-[(3-cyclopropyl-1H-pyrazol-5-yl)amino]-6-methylpyrimidin-2-yl}piperidine-3-carboxylate

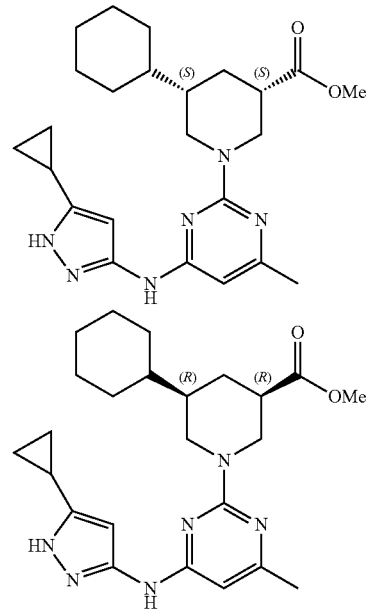

Methyl cis-5-cyclohexyl-1-{4-[(3-cyclopropyl-1H-pyrazol-5-yl)amino]-6-methylpyrimidin-2-yl}piperidine-3-carboxylate (46.4 mg) prepared in Step 1 of Example 17 was separated and purified on HPLC (mobile phase; hexane/isopropanol/diethylamine=50/10/0.06, flow rate; 23 ml/min) using CHIRALCEL° OD-H (φ2 cm×25 cm, DAICEL). (3S*, 5S*)-isomer (21.8 mg, optical purity: >99% d.e.) and (3R*, 5R*)-isomer (20.6 mg, optical purity: 943% d.e.) were obtained from the less polar fraction and from the polar fraction, respectively.

Here the S* and R* symbols are provisionally assigned, because their stereo structures has not been specified, and d.e. is an abbreviation for diastereomer excess.

EXAMPLE 20

Preparation of (3S*,5S*)-5-cyclohexyl-1-{4-[(3-cyclopropyl-1H-pyrazol-5-yl)amino]-6-methylpyrimidin-2-yl}piperidine-3-carboxylic acid trifluoroacetate

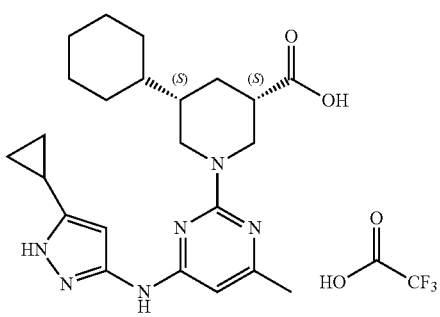

The title compound was prepared by the similar manner described in Example 10 using methyl (3S*,5S*)-5-cyclohexyl-1-{4-[(3-cyclopropyl-1H-pyrazol-5-yl)amino]-6-methylpyrimidin-2-yl}piperidine-3-carboxylate prepared in Example 18 instead of methyl cis-1-[4-methyl-6-(1H-pyrazol-5-ylamino)pyrimidin-2-yl]-5-phenylpiperidine-3-carboxylate trifluoroacetate.

$^1$H NMR (400 MHz, DMSO-$d_6$) δ 0.69-0.78 (2H, m), 0.95-1.04 (2H, m), 1.04-1.38 (7H, m), 1.38-1.54 (2H, m), 1.64-1.73 (1H, m), 1.73-1.86 (4H, m), 1.86-1.94 (1H, m), 2.22-2.33 (1H, m), 2.37 (3H, s), 2.53-2.67 (1H, m), 2.73-2.90 (1H, m), 3.02-3.18 (1H, m), 4.40-4.85 (2H, br), 6.11 (1H, brs), 6.30 (1H, brs)

ESI-MS m/z 425.4 [M+H]$^+$.

EXAMPLE 21

Preparation of (3R*,5R*)-5-cyclohexyl-1-{4-[(3-cyclopropyl-1H-pyrazol-5-yl)amino]-6-methylpyrimidin-2-yl}piperidine-3-carboxylic acid trifluoroacetate The title compound was prepared by the similar manner described in Example 10 using methyl (3R*,5R*)-5-cyclohexyl-1-{4-[(3-cyclopropyl-1H-pyrazol-5-yl)amino]-6-methylpyrimidin-2-yl}piperidine-3-carboxylate prepared in Example 19 instead of methyl cis-1-[4-methyl-6-(1H-pyrazol-5-ylamino)pyrimidin-2-yl]-5-phenylpiperidine-3-carboxylate trifluoroacetate.

$^1$H NMR (400 MHz, DMSO-$d_6$) δ 0.69-0.78 (2H, m), 0.95-1.04 (2H, m), 1.04-1.38 (7H, m), 1.38-1.54 (2H, m), 1.64-1.73 (1H, m), 1.73-1.86 (4H, m), 1.86-1.94 (1H, m), 2.22-2.33 (1H, m), 2.37 (3H, s), 2.53-2.67 (1H, m), 2.73-2.90 (1H, m), 3.02-3.18 (1H, m), 4.40-4.85 (2H, br), 6.11 (1H, brs), 6.30 (1H, brs)

ESI-MS m/z 425.4 [M+H]$^+$.

Here the S* and R* symbols are provisionally assigned, because their stereo structures has not been specified.

EXAMPLE 22

Preparation of (cis-5-cyclohexyl-1-{4-[(3-cyclopropyl-1H-pyrazol-5-yl)amino]-6-methylpyrimidin-2-yl}piperidin-3-yl)acetic acid trifluoroacetate

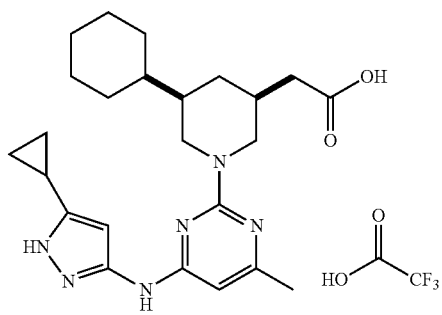

Step 1: Preparation of tert-butyl cis-3-cyclohexyl-5-(hydroxymethyl)piperidine-1-carboxylate

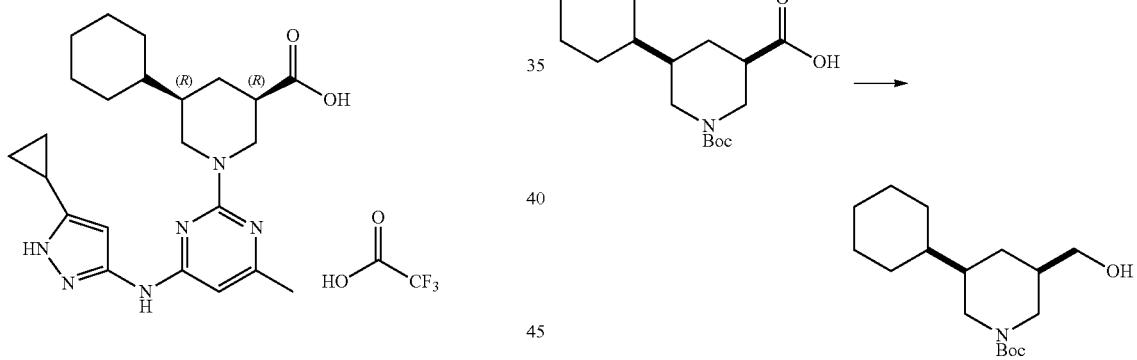

To the solution of cis-1-(tert-butoxycarbonyl)-5-cyclohexylpiperidine-3-carboxylic acid (400.9 mg) in THF (10 ml) was added 2 M solution of borane dimethylsulfide complex in THF (4.0 ml) at −15° C. under stirring. After stirring for 4 hours, The mixture was quenched by addition of MeOH. The resulting mixture was allowed to be room temperature and concentrated. To the residue was added saturated aqueous solution of NH$_4$Cl and extracted with EtOAc. The extract was washed with brine, dried over MgSO$_4$ and concentrated. The residue was purified with silica gel column chromatography (eluent: CHCl$_3$/MeOH=99/1~90/10) to give tert-butyl cis-3-cyclohexyl-5-(hydroxymethyl)piperidine-1-carboxylate (505.1 mg) as a colorless oil.

$^1$H NMR (400 MHz, CDCl$_3$) δ 0.82 (1H, q), 0.90-1.33 (7H, m), 1.45 (9H, s), 1.59-1.87 (6H, m), 1.84-1.92 (1H, m), 1.98 (1H, s), 2.30 (1H, td), 3.43-3.55 (2H, m), 1.17 (1H, tt)

EST-MS m/z 198.6 [M+H]$^+$.

Step 2: Preparation of tert-butyl cis-3-(cyanomethyl)-5-cyclohexylpiperidine-1-carboxylate

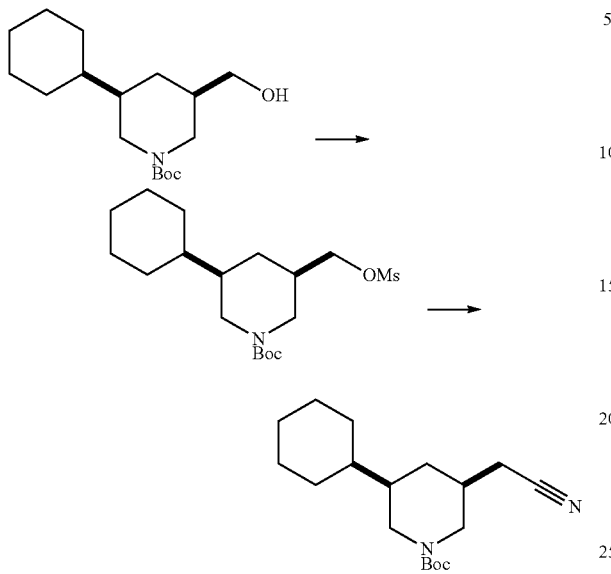

To the solution of tert-utyl cis-3-cyclohexyl-5-(hydroxymethyl)piperidine-1-carboxylate (431.1 mg) in THF (10 ml) was added TEA (405.0 ml) and MsCl (135.2 ml) at 0° C. After stirring at 0° C. for 1 hour, the insoluble material was filtered off through celite and washed with THF. The filtrate was concentrated to give the crude tert-butyl cis-3-cyclohexyl-5-{[(methylsulfonyl)oxy]methyl}piperidine-1-carboxylate as a pale brown oil.

The mixture of the crude mesylate and KCN (0.258 g) in DMF (6 ml) was heated to 80° C. under stirring. After 4 hours, the mixture was cooled to room temperature, poured into saturated aqueous solution of NaHCO₃ and extracted with EtOAc. The extract was washed with brine, dried over Na₂SO₄ and concentrated. The residue was purified with silica gel column chromatography (eluent: hexane/EtOAc=92/8~40/60) to give tert-butyl cis-3-cyanomethyl-5-cyclohexylpiperidine-1-carboxylate (328.2 mg) as a colorless oil.

¹H NMR (400 MHz, CDCl₃) δ 0.90-1.07 (3H, m), 1.10-1.37 (5H, m), 1.46 (9H, s), 1.62-1.88 (6H, m), 1.97-2.05 (1H, m), 2.21-2.42 (4H, m), 4.06-4.26 (2H, m)

Step 3: Preparation of methyl (cis-5-cyclohexylpiperidine-3-yl)acetate hydrochloride

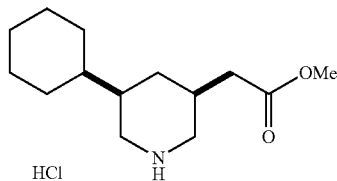

To the solution of tert-butyl cis-3-cyanomethyl-5-cyclohexylpiperidine-1-carboxylate (116.7 mg) in MeOH (6 ml) was added conc HCl (6 ml). And the mixture was heated to reflux temperature under stirring for 10 hours. The resulting mixture was cooled to room temperature and concentrated. The residue was dissolved into 10% solution of HCl in MeOH (6 ml) and the solution was stirred at room temperature for 3 hours and concentrated to give the crude methyl (cis-5-cyclohexylpiperidine-3-yl)acetate hydrochloride as a colorless solid.

ESI-MS m/z 240.6 [M+H]⁺.

Step 4: Preparation of methyl (cis-5-cyclohexyl-1-{4-[(3-cyclopropyl-1H-pyrazol-5-yl)amino]-6-methylpyrimidin-2-yl}piperidin-3-yl)acetate

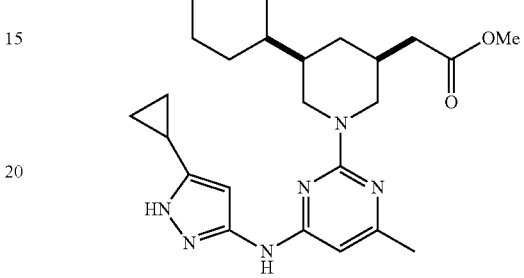

The title compound was prepared by the similar manner described in Example 1 using methyl (cis-5-cyclohexylpiperidine-3-yl)acetate hydrochloride instead of (S)-3-(tert-butoxycarbonylamino)piperidine, and 2-chloro-N-(3-cyclopropyl-1H-pyrazol-5-yl)-6-methylpyrimidin-4-amine prepared in Referential Example 2 instead of 2-chloro-6-methyl-N-(1H-pyrazol-5-yl)pyrimidin-4-amine.

ESI-MS m/z 430.4 [M+H]⁺.

Step 5: Preparation of (cis-5-cyclohexyl-1-{4-[(3-cyclopropyl-1H-pyrazol-5-yl)amino]-6-methylpyrimidin-2-yl}piperidin-3-yl)acetic acid trifluoroacetate

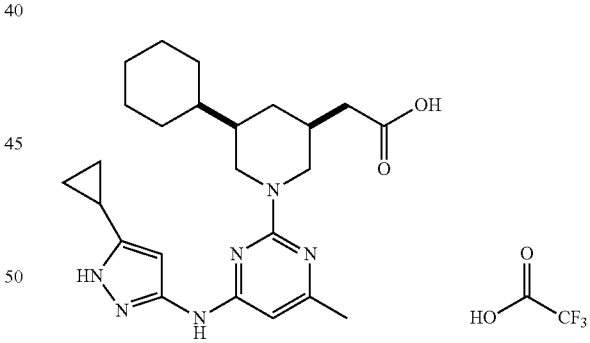

The title compound was prepared by the similar manner described in Example 10 using methyl (cis-5-cyclohexyl-1-{4-[(3-cyclopropyl-1H-pyrazol-5-yl)amino]-6-methylpyrimidin-2-yl}piperidin-3-yl)acetate prepared in Step 4 instead of methyl cis-1-[4-methyl-6-(1H-pyrazol-5-ylamino)pyrimidin-2-yl]-5-phenylpiperidine-3-carboxylate trifluoroacetate.

¹H NMR (400 MHz, CD₃OD) δ 0.71-0.77 (2H, m), 1.01 (2H, dq), 1.02-1.35 (7H, m), 1.39-1.52 (1H, m), 1.63-1.72 (1H, m), 1.72-1.85 (4H, m), 1.88-2.08 (3H, m), 2.24-2.42 (2H, m), 2.35 (3H, s), 2.62-2.86 (2H, m), 4.15-5.20 (2H, br), 5.67-6.88 (2H, m)

ESI-MS m/z 439.3 [M+H]⁺.

EXAMPLE 23

Preparation of [(3S*,5R*)-5-cyclohexyl-1-{4-[(3-cyclopropyl-1H-pyrazol-5-yl)amino]-6-methylpyrimidin-2-yl}piperidin-3-yl]acetic acid

EXAMPLE 24

Preparation of [(3R*,5S*)-5-cyclohexyl-1-{4-[(3-cyclopropyl-1H-pyrazol-5-yl)amino]-6-methylpyrimidin-2-yl}piperidin-3-yl]acetic acid

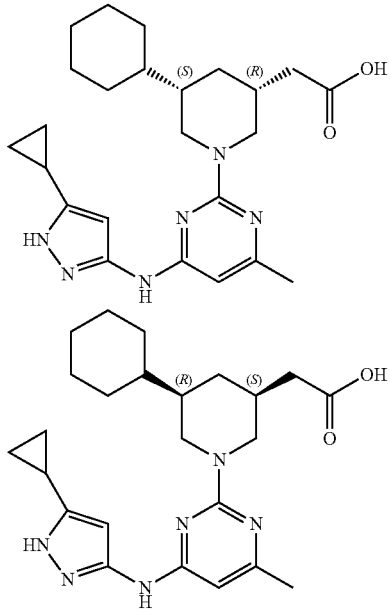

(cis-5-Cyclohexyl-1-{4-[(3-cyclopropyl-1H-pyrazol-5-yl)amino]-6-methylpyrimidin-2-yl}piperidin-3-yl)acetic acid trifluoroacetate (16.5 mg) prepared in Step 5 of Example 21 was separated and purified on HPLC (mobile phase; hexane/ethanol/diethylamine=70/30/0.1, flow rate; 25 ml/min) using CHIRALPAK® (φ2 cm×25 cm, DAICEL). (3S*,5R*)-isomer (4.5 mg) and (3R*,5S*)-isomer (5.5 mg) were obtained from the less polar fraction and from the polar fraction, respectively.

Here the S* and R* symbols are provisionally assigned, because their stereo structures has not been specified.

EXAMPLE 25

Preparation of {cis-5-cyclohexyl-1-[4-methyl-6-(1,3-thiazol-2-ylamino)pyrimidin-2-yl]piperidin-3-yl}acetic acid

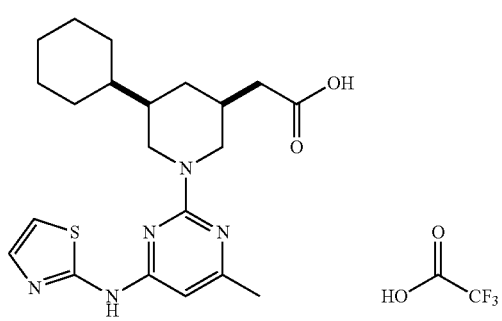

Step 1: Preparation of methyl {cis-5-cyclohexyl-1-[4-methyl-6-(1,3-thiazol-2-ylamino)pyrimidin-2-yl]piperidin-3-yl}acetate

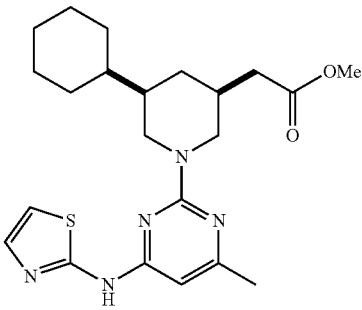

The title compound was prepared by the similar manner described in Example 1 using methyl (cis-5-cyclohexylpiperidine-3-yl)acetate hydrochloride prepared in Step 3 of Example 22 instead of (S)-3-(tert-butoxycarbonylamino)piperidine, and 2-chloro-6-methyl-N-(1,3-thiazol-2-yl)pyrimidin-4-amine prepared in Referential Example 3 instead of 2-chloro-6-methyl-N-(1H-pyrazol-5-yl)pyrimidin-4-amine.

ESI-MS m/z 430.4 [M+H]$^+$.

Step 2: Preparation of {cis-5-cyclohexyl-1-[4-methyl-6-(1,3-thiazol-2-ylamino)pyrimidin-2-yl]piperidin-3-yl}acetic acid

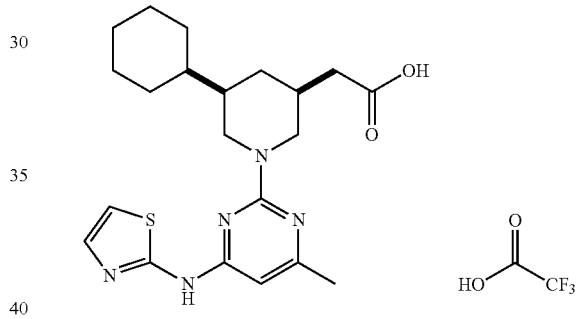

The title compound was prepared by the similar manner described in Example 10 using methyl {cis-5-cyclohexyl-1-[4-methyl-6-(1,3-thiazol-2-ylamino)pyrimidin-2-yl]piperidin-3-yl}acetate prepared in Step 1 instead of methyl cis-1-[4-methyl-6-(1H-pyrazol-5-ylamino)pyrimidin-2-yl]-5-phenylpiperidine-3-carboxylate trifluoroacetate.

$^1$H NMR (400 MHz, CD$_3$OD) δ 0.98-1.40 (7H, m), 1.46-1.61 (1H, m), 1.61-1.91 (5H, m), 1.95-2.15 (2H, m), 2.25-2.45 (2H, m), 2.41 (3H, s), 2.68-2.97 (2H, m), 3.70-5.70 (2H, br), 6.26 (1H, s), 7.25 (1H, d), 7.51 (1H, d)

ESI-MS m/z 416.5 [M+H]$^+$.

REFERENTIAL EXAMPLES

REFERENTIAL EXAMPLE 1

Preparation of 2-chloro-6-methyl-N-(1H-pyrazol-5-yl)pyrimidin-4-amine

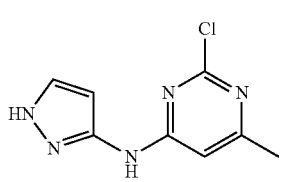

To the solution of 2,4-dichloro-6-methylpyrimidine (3.00 g) and 1H-pyrazol-5-amine (1.31 g) in NMP (30 ml) was added NaI (2.36 g) and DIEA (6.33 ml). And the mixture was heated to 80° C. under stirring. After 1 day, the mixture was cooled to room temperature. The mixture was diluted with EtOAc. The precipitate was collected by filtration, washed with the mixed solvent of hexane and EtOAc and dried in vacuo to give 2-chloro-6-methyl-N-(1H-pyrazol-5-yl)pyrimidin-4-amine (2.60 g) as a pale pink solid.

REFERENTIAL EXAMPLE 2

Preparation of 2-chloro-N-(3-cyclopropyl-1H-pyrazol-5-yl)-6-methylpyrimidin-4-amine

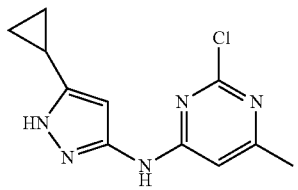 [SMILES: Cc1cc(Nc2cc(C3CC3)[nH]n2)nc(Cl)n1]

To the solution of 2,4-dichloro-6-methylpyrimidine (1.63 g) and 3-cyclopropyl-1H-pyrazol-5-amine (1.24 g) in DMF (20 ml) was added NaI (1.49 g) and DIEA (1.72 ml). And the mixture was stirred at 80° C. overnight. The mixture was concentrated to remove DMF. The residue was suspended into EtOAc. The insoluble material was filtered off and washed with EtOAc. The filtrate was concentrated and the residue was pufiried with silica gel column chromatography (eluent: $CHCl_3$/MeOH=98/2~90/10) to give 2-chloro-N-(3-cyclopropyl-1H-pyrazol-5-yl)-6-methylpyrimidin-4-amine (1054 mg) as a pale pink solid.

$^1$H NMR (400 MHz, $CDCl_3$) δ 0.70-0.76 (2H, m), 0.96-1.03 (2H, m), 1.83-1.91 (1H, m), 2.36 (3H, s), 5.84 (1H, brs), 6.94 (1H, brs), 8.05 (1H, brs)

ESI-MS m/z 250.1 $[M+H]^+$.

REFERENTIAL EXAMPLE 3

Preparation of 2-chloro-6-methyl-N-(1,3-thiazol-2-yl)pyrimidin-4-amine

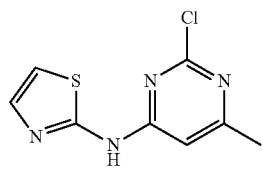

To the mixture of 2,4-dichloro-6-methylpyrimidine (507.7 mg), 1,3-thiazol-2-amine (345.0 mg), 4,5-bis(diphenylphosphino)-9,9-dimethylxanthene (289.1 mg) and $K_3PO_4$ (936.3 mg) in dioxane (20 ml) was added $Pd_2(dba)_3$·$CHCl_3$ (255.9 mg). And the suspension was stirred at 85° C. overnight. The mixture was cooled to room temperature. The insoluble material was filtered off and washed with EtOAc. The filtrate was poured into saturated aqueous solution of $NaHCO_3$ and extracted with EtOAc. The extract was washed with brine, dried over $Na_2SO_4$ and concentrated. The residue was purified with silica gel column chromatography (eluent: $CHCl_3$/MeOH=98/2~90/10) to give 2-chloro-6-methyl-N-(1,3-thiazol-2-yl)pyrimidin-4-amine as an orange solid.

$^1$H NMR (400 MHz, $CDCl_3$) δ 2.48 (3H, s), 6.69 (1H, s), 7.07 (1H, d), 7.52 (1H, d)

ESI-MS m/z 227.1 $[M+H]^+$.

REFERENTIAL EXAMPLE 4

Preparation of 2-chloro-N-(5-cyclopropyl-1,3-thiazol-2-yl)-6-methylpyrimidin-4-amine

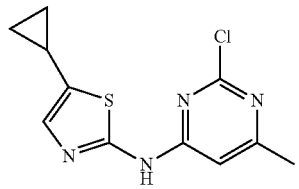 [SMILES: Cc1cc(Nc2ncc(C3CC3)s2)nc(Cl)n1]

The title compound was prepared by the similar manner described in Referential Example 3 using 5-cyclopropyl-1,3-thiazol-2-amine instead of 1,3-thiazol-2-amine:

$^1$H NMR (400 MHz, DMSO-$d_6$) δ 0.66 (2H, m), 0.94 (2H, m), 2.02 (1H, m), 2.33 (3H, s), 6.81 (1H, s), 7.15 (1H, s), 11.84 (1H, s)

ESI-MS m/z 267.4 $[M+H]^+$.

REFERENTIAL EXAMPLE 5

Preparation of 2-[(2-chloro-6-methylpyrimidin-4-yl)amino]-1,3-thiazole-5-carbonitrile

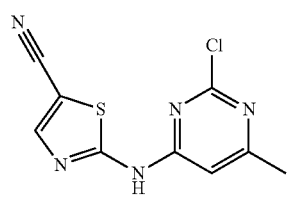 [SMILES: Cc1cc(Nc2ncc(C#N)s2)nc(Cl)n1]

The title compound was prepared by the similar manner described in Referential Example 3 using 2-amino-1,3-thiazole-5-carbonitrile instead of 1,3-thiazol-2-amine.

$^1$H NMR (400 MHz, DMSO-$d_6$) δ 2.41 (3H, s), 6.91 (1H, s), 8.38 (1H, s), 12.89 (1H, s)

ESI-MS m/z 252.4 $[M+H]^+$.

INDUSTRIAL APPLICABILITY

The compound of the invention exhibits excellent Aurora A selective inhibitory action, and thus it is expected as a useful antitumor agent in the field of pharmaceuticals.

What is claimed is:

1. A compound of Formula (I):

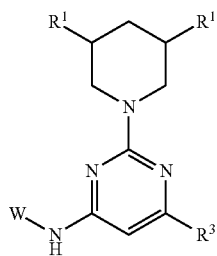

(I)

wherein:

$R^1$ is H, —NHCOOR$^{1a}$, $C_{5-6}$ cycloalkyl, or phenyl, where the cycloalkyl and phenyl each independently may be substituted with one to three of the same or different substituents selected from $R^{10}$);

$R^{1a}$ is $C_{1-3}$ alkyl which may be substituted with one to three of the same or different substituents selected from F and Cl;

$R^2$ is H, —COOH, —CH$_2$ COOH, —COOR$^{2a}$, or —CH$_2$COOR$^{2a}$;

$R^{2a}$ is $C_{1-2}$ alkyl, where the alkyl may be substituted with one to three of the same or different substituents selected from halogen atoms;

$R^3$ is H, $C_{1-6}$ alkyl, where the alkyl may be substituted with one to three of the same or different substituents selected from $R^{11}$;

$R^{10}$ is F, Cl, CF$_3$, or $C_{1-2}$ alkyl;

$R^{11}$ is halogen atom, hydroxy, or cyano;

W is selected from:

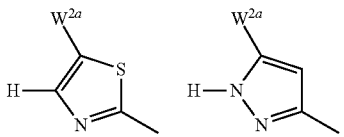

$W^{2a}$ is H, halogen atom, cyano, or $C_{3-5}$ cycloalkyl, or a pharmaceutically acceptable salt thereof.

2. The compound according to claim 1 or a pharmaceutically acceptable salt thereof, wherein $R^2$ is —COOH or —CH$_2$ COOH.

3. The compound according to claim 2 or a pharmaceutically acceptable salt or ester thereof, wherein:

$R^1$ is —NHCOOR$^{1a}$, cyclohexyl, or phenyl, where the cyclohexyl and phenyl each independently may be substituted with one to three of the same or different substituents selected from $R^{10}$;

$R^{1a}$ is methyl, ethyl, propyl, isopropyl, or t-butyl, any of which may be substituted with one to three of fluorine atoms; and $R^{10}$ is F or Cl.

4. The compound according to claim 3 or a pharmaceutically acceptable salt thereof, wherein $W^{2a}$ is H, cyano, or cyclopropyl.

5. A compound which is:
  (a) methyl trans-5-[(tert-butoxycarbonyl)amino]-1-[4-methyl-6-(1H-pyrazol-5-ylamino)pyrimidin-2-yl]piperidine-3-carboxylate;
  (b) trans-5-[(tert-butoxycarbonyl)amino]-1-[4-methyl-6-(1H-pyrazol-5-ylamino)pyrimidin-2-yl]piperidine-3-carboxylic acid;
  (c) methyl cis-5-[(tert-butoxycarbonyl)amino]-1-[4-methyl-6-(1H-pyrazol-5-ylamino)pyrimidin-2-yl]piperidine-3-carboxylate;
  (d) cis-5-[(tert-butoxycarbonyl)amino]-1-[4-methyl-6-(1H-pyrazol-5-ylamino)pyrimidin-2-yl]piperidine-3-carboxylic acid;

(e) methyl trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylate;

(f) trans-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(g) methyl cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(h) cis-1-[4-methyl-6-(1H-pyrazol-5-ylamino)pyrimidin-2-yl]-5-[({[(2S)-1,1,1-trifluoropropan-2-yl]oxy}carbonyl)amino]piperidine-3-carboxylic acid;

(i) methyl cis-1-[4-methyl-6-(1H-pyrazol-5-ylamino)pyrimidin-2-yl]-5-phenylpiperidine-3-carboxylate;

(j) cis-1-[4-methyl-6-(1H-pyrazol-5-ylamino)pyrimidin-2-yl]-5-phenylpiperidine-3-carboxylic acid;

(k) methyl cis-1-[4-methyl-6-(1H-pyrazol-5-ylamino)pyrimidin-2-yl]-5-[3-(trifluoromethyl)phenyl]piperidine-3-carboxylate;

(l) cis-1-[4-methyl-6-(1H-pyrazol-5-ylamino)pyrimidin-2-yl]-5-[3-(trifluoromethyl)phenyl]piperidine-3-carboxylic acid;

(m) methyl cis-5-cyclohexyl-1-[4-methyl-6-(1H-pyrazol-5-ylamino)pyrimidin-2-yl]piperidine-3-carboxylate;

(n) cis-5-cyclohexyl-1-[4-methyl-6-(1H-pyrazol-5-ylamino)pyrimidin-2-yl]piperidine-3-carboxylic acid;

(o) methyl cis-5-cyclohexyl-1-[4-methyl-6-(1,3-thiazol-2-ylamino)pyrimidin-2-yl]piperidine-3-carboxylate;

(p) cis-5-cyclohexyl-1-[4-methyl-6-(1,3-thiazol-2-ylamino)pyrimidin-2-yl]piperidine-3-carboxylic acid;

(q) methyl cis-1-{4-[(5-cyano-1,3-thiazol-2-yl)amino]-6-methylpyrimidin-2-yl}-5-cyclohexylpiperidine-3-carboxylate;

(r) cis-1-{4-[(5-cyano-1,3-thiazol-2-yl)amino]-6-methylpyrimidin-2-yl}-5-cyclohexylpiperidine-3-carboxylic acid;

(s) methyl cis-5-cyclohexyl-1-{4-[(5-cyclopropyl-1,3-thiazol-2-yl)amino]-6-methylpyrimidin-2-yl}piperidine-3-carboxylate;

(t) cis-5-cyclohexyl-1-{4-[(5-cyclopropyl-1,3-thiazol-2-yl)amino]-6-methylpyrimidin-2-yl}piperidine-3-carboxylic acid;

(u) methyl cis-5-cyclohexyl-1-{4-[(3-cyclopropyl-1H-pyrazol-5-yl)amino]-6-methylpyrimidin-2-yl}piperidine-3-carboxylate;

(v) cis-5-cyclohexyl-1-{4-[(3-cyclopropyl-1H-pyrazol-5-yl)amino]-6-methylpyrimidin-2-yl}piperidine-3-carboxylic acid;

(w) methyl (cis-5-cyclohexyl-1-{4-[(3-cyclopropyl-1H-pyrazol-5-yl)amino]-6-methylpyrimidin-2-yl}piperidin-3-yl)acetate;

(x) (cis-5-cyclohexyl-1-{4-[(3-cyclopropyl-1H-pyrazol-5-yl)amino]-6-methylpyrimidin-2-yl}piperidin-3-yl)acetic acid;

(y) methyl {cis-5-cyclohexyl-1-[4-methyl-6-(1,3-thiazol-2-ylamino)pyrimidin-2-yl]piperidin-3-yl}acetate, or (z) {cis-5-cyclohexyl-1-[4-methyl-6-(1,3-thiazol-2-ylamino)pyrimidin-2-yl]piperidin-3-yl}acetic acid, or a pharmaceutically acceptable salt thereof.

6. A pharmaceutical composition comprising, together with pharmaceutically acceptable carrier or diluent, at least one compound according to claim 1 as active ingredient.

\* \* \* \* \*

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Ala Leu Arg Arg Ala Ser Leu Gly
 1               5

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Leu Arg Arg Ala Ser Leu Gly
 1               5
```